(12) United States Patent
Giuliani et al.

(10) Patent No.: US 10,598,666 B2
(45) Date of Patent: Mar. 24, 2020

(54) IN VITRO POTENCY ASSAY FOR PROTEIN-BASED MENINGOCOCCAL VACCINES

(71) Applicant: GlaxoSmithKline Biologicals SA, Rixensart (BE)

(72) Inventors: Marzia Giuliani, Siena (IT); Elena Mori, Monteriggioni (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 0 days.

(21) Appl. No.: 14/382,690

(22) PCT Filed: Mar. 8, 2013

(86) PCT No.: PCT/EP2013/054670
§ 371 (c)(1),
(2) Date: Sep. 3, 2014

(87) PCT Pub. No.: WO2013/132040
PCT Pub. Date: Sep. 12, 2013

(65) Prior Publication Data
US 2015/0301051 A1    Oct. 22, 2015

Related U.S. Application Data

(60) Provisional application No. 61/608,293, filed on Mar. 8, 2012.

(51) Int. Cl.
| C07K 16/12 | (2006.01) |
| G01N 33/577 | (2006.01) |
| A61K 39/095 | (2006.01) |
| G01N 33/569 | (2006.01) |

(52) U.S. Cl.
CPC ....... *G01N 33/577* (2013.01); *C07K 16/1217* (2013.01); *G01N 33/56911* (2013.01); *C07K 2317/33* (2013.01); *C07K 2317/56* (2013.01); *G01N 2333/22* (2013.01)

(58) Field of Classification Search
CPC ......... G01N 2333/22; G01N 33/56911; G01N 33/577; G01N 33/15; C07K 16/1217; C07K 2317/33; C07K 2317/56; A61K 2039/6037; A61K 2039/6068; A61K 39/095
See application file for complete search history.

(56) References Cited

U.S. PATENT DOCUMENTS

| 4,525,452 A | 6/1985 | Jones et al. |
| 5,698,438 A | 12/1997 | Stoiljkovic et al. |
| 6,180,111 B1 | 1/2001 | Stein et al. |
| 7,368,261 B1 | 5/2008 | Rappuoli |
| 7,510,687 B2 | 3/2009 | Mazzeo et al. |
| 7,576,176 B1 | 8/2009 | Fraser et al. |
| 8,722,062 B2 | 5/2014 | Ryall |

| 2009/0285845 A1* | 11/2009 | Masignani | C07K 14/22 424/190.1 |
| 2010/0035234 A1* | 2/2010 | Donnelly | G01N 33/53 435/5 |
| 2013/0196352 A1* | 8/2013 | Balocchi | A61K 39/095 435/7.72 |

FOREIGN PATENT DOCUMENTS

| EP | 0011243 B1 | 4/1982 |
| WO | WO-96/29412 A1 | 9/1996 |
| WO | WO-99/57280 A2 | 11/1999 |
| WO | WO-00/23595 A | 4/2000 |
| WO | WO-00/66741 A2 | 11/2000 |
| WO | WO-2000/077518 A2 | 12/2000 |
| WO | WO-01/34642 A2 | 5/2001 |
| WO | WO-01/38350 A2 | 5/2001 |
| WO | WO-01/40473 A2 | 6/2001 |
| WO | WO-01/55182 A1 | 8/2001 |
| WO | WO-01/91788 A1 | 12/2001 |
| WO | WO-02/09643 A2 | 2/2002 |
| WO | WO-03/063766 A2 | 8/2003 |
| WO | WO-2003/069342 A1 | 8/2003 |
| WO | WO-03/105890 A2 | 12/2003 |
| WO | WO-2004/019977 A2 | 3/2004 |
| WO | WO-04/048404 A2 | 6/2004 |
| WO | WO-2005/004908 A1 | 1/2005 |
| WO | WO-05/032583 A2 | 4/2005 |
| WO | WO-2006/024946 A2 | 3/2006 |

(Continued)

OTHER PUBLICATIONS

Vu et al. Scientific Reports 2: 341, Mar. 28, 2012.*
Castro et al. Rev. Cubana Farm. 43: Cuidad de la Habana, Sep.-Nov. 2009, Original.*
English translated Castro et al. Rev. Cubana Farm. 43: Cuidad de la Habana, Sep.-Nov. 2009.*
Pajon et al. Infect. Immun. 80: 2677-2687, online pub May 21, 2012.*
Borrow et al. (2005) "Interlaboratory standardization of the measurement of serum bactericidal activity by using human complement against meningococcal serogroup b, strain 44/76-SL, before and after vaccination with the Norwegian MenBvac outer membrane vesicle vaccine." Clin Diag Lab Immunol 12:970-6.

(Continued)

*Primary Examiner* — Sarvamangala Devi

(57) ABSTRACT

The invention uses ELISA or similar assays for analysing a meningococcal vaccine. The assay uses antibodies which bind to meningococcal proteins within the vaccine, and in particular monoclonal antibodies which are bactericidal for meningococcus and/or which recognise conformational epitopes within the meningococcal proteins. By performing the assay on a series of dilutions of a test vaccine, and by comparing the results with those obtained using a reference vaccine of known potency, it is possible to determine the relative potency of the test vaccine. This value can be used as a parameter for determining whether a manufactured batch of a vaccine is suitable for release to the public, or whether it has experienced a production failure and so should not be used.

11 Claims, 8 Drawing Sheets

Specification includes a Sequence Listing.

(56) References Cited

FOREIGN PATENT DOCUMENTS

| WO | WO-2006/034320 A2 | 3/2006 |
|---|---|---|
| WO | WO-2006/046143 A2 | 5/2006 |
| WO | WO-2007/054820 A2 | 5/2007 |
| WO | WO-2007/066231 A2 | 6/2007 |
| WO | WO-2009/104097 A2 | 8/2009 |
| WO | WO-2009/143168 A2 | 11/2009 |
| WO | WO 2009/143168 A2 * | 11/2009 |
| WO | WO-2009/150531 A1 | 12/2009 |
| WO | WO-2009/158142 A1 | 12/2009 |
| WO | WO-2010/070453 A2 | 6/2010 |
| WO | WO-2011/036562 A1 | 3/2011 |
| WO | WO-2011/110634 A1 | 9/2011 |

OTHER PUBLICATIONS

Borrow et al. (2006) "Neisseria meningitidis group B correlates of protection and assay standardization—international meeting report Emory University, Atlanta, Georgia, United States, Mar. 16-17, 2005." Vaccine. 24:5093-107.

Chatterjee et al. (2010). "The immunogenicity and safety of a reduced PRP-content DTPw-HBV/Hib vaccine when administered according to the accelerated EPI schedule," BMC Infect Dis, 10:298.

Comanducci, M. (2002). "NadA, a Novel Vaccine Candidate of Neisseria Meningitides," Journal of Experimental Medicine 195(11):1445-1454.

Donnelly et al. (2010). "Qualitative and quantitative assessment of meningococcal antigens to evaluate the potential strain coverage of protein-based vaccines," Proc Natl Acad Sci U S A, 107(45):19490-5.

Drow et al. (1979). "Indirect sandwich enzyme-linked immunosorbent assay for rapid detection of Haemophilus influenzae type b infection," J Clin Microbiol, 10(4):442-50.

Findlow et al. (2006). "Comparison and Correlation of Neisseria meningitidis Serogroup B Immunologic Assay Results and Human Antibody Responses following Three Doses of the Norwegian Meningococcal Outer Membrane Vesicle Vaccine MenBvac", Infection and Immunity 74(8):4557-4565.

Frasch, C. et al. (Jun. 2009) "Bactericidal Antibody is the Immunologic Surrogate of Protection Against Meningococcal Disease," Vaccine 27( Suppl 2):B112-B116.

Giuliani et al. (2006). "A universal vaccine for serogroup B meningococcus," PNAS 103(29):10834-10839.

Granoff, D. (Dec. 2001) "Assessing Efficacy of Haemophilus Influenzae Type B Combination Vaccines," Clinical Infectious Diseases: An Official Publication of the Infectious Diseases Society of America 33(Suppl 4):S278-S287.

Granoff, D. and Harris, S. (Jun. 2004) "Protective Activity of Group C Anticapsular Antibodies Elicited in Two-year-olds by an Investigational Quadrivalent Neisseria Meningitidis-Diphtheria Toxoid Conjugate Vaccine," The Pediatric Infectious Disease Journal 23(6):490-497.

Hou et al. (2005) "Protective antibody responses elicited by a meningococcal outer membrane vesicle vaccine with overexpressed genome-derived neisserial antigen 1870," J Infect Dis 192(4):580-90.

Invitation to Pay Additional Fees dated Oct. 8, 2009, for PCT Application No. PCT/US2009/044539, filed May 19, 2009, 15 pages.

Joder, L. et al. (Jul. 2003) "Serological Criteria for Evaluation and Licensure of New Pneumococcal Conjugate Vaccine Formulations for Use in Infants," Vaccine 21(23):3265-3272.

Joseph et al. (2004). "Assignment of Neisseria meningitidis serogroups A, C, W135, and Y anticapsular total immunoglobulin G (IgG), IgG1, and IgG2 concentrations to reference sera," Clin Diagn Lab Immunol, 11(1):1-5.

Li, S. et al. (Apr. 2002) "Inverse Relationship Between Six Week Postvaccination Varicella Antibody Response to Vaccine and Likelihood of Long Term Breakthrough Infection," The Pediatrician Infectious Disease Journal 21(4):337-342.

Masignani V. (Mar. 17, 2003). "Vaccination against Neisseria meningitidis using three variants of the lipoprotein GNA1870," J. Exp. Med. 197(6):789-799.

Miura, K. et al. (Aug. 2007) "Transmission-Blocking Activity Induced by Malaria Vaccine Candidates Pfs25/Pvs25 is a Direct and Predictable Function of Antibody Titer," Malaria Journal 6(1):107.

Moe, et al. (2002). "Sequential immunization with vesicles prepared from heterologous Neisseria meningitidis strains elicits broadly protective serum antibodies to group B strains," Infect Immun 70(11):6021-6031.

Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.

Poirier et al. (2000). "In vitro potency assay for hepatitis A vaccines: development of a unique economical test," Biologicals, 28(4):247-56.

Qin, L. et al. (Nov. 2007) "A Framework for Assessing Immunological Correlates of Protection in Vaccine Trials," The Journal of Infectious Diseases 196(9):1304-1312.

Rosenqvist et al. (1990). "Serogroup determination of Neisseria meningitidis by whole-cell ELISA, dot-blotting and agglutination," APMIS: acta pathologica, microbiologica, et immunologica Scandinavica 98(6):501-506.

Sarafian et al. (1982). "Detection of gonococcal antigens by an indirect sandwich enzyme-linked immunosorbent assay," J Med Microbiol, 15(4):541-50.

Serruto et al. (2010). "Neisseria meningitidis GNA2132, a heparin-binding protein that induces protective immunity in humans," PNAS 107(8):3770-3775.

Shin, S. et al. (Dec. 2005) "A Predictive Model for the Level of sIgA Based on IgG Levels Following the Oral Administration of Antigens Expressed in *Saccharomyces cerevisiae*," Journal of Veterinary Science 6(4):305-309.

Sippel et al. (1984). "Detection of Neisseria meningitidis group A, Haemophilus influenzae type b, and *Streptococcus pneumoniae* antigens in cerebrospinal fluid specimens by antigen capture enzyme-linked immunosorbent assays," J Clin Microbiol, 20(2):259-65.

Spellberg, B. et al. (Apr. 2008) "Antibody Titer Threshold Predicts Anti-Candidal Vaccine Efficacy Even Though the Mechanism of Protection is Induction of Cell-Mediated Immunity," The Journal of Infectious Diseases 197(7):967-971.

Strady, C. et al. (Jun. 2000) "Predictive Factors for the Neutralizing Antibody Response Following Pre-exposure Rabies Immunization: Validation of a New Booster Dose Strategy," Vaccine 18(24):2661-2667.

Sugasawara et al. (1984). "Enzyme-linked immunosorbent assay with a monoclonal antibody for detecting group A meningococcal antigens in cerebrospinal fluid," J Clin Microbiol. 19(2):230-4.

Tsang et al. (2005). "Serological specificities of murine hybridoma monoclonal antibodies against Neisseria meningitidis serogroups B, C, Y, and W135 and evaluation of their usefulness as serogrouping reagents by indirect whole-cell enzyme-linked immunosorbent assay," Clin Diagn Lab Immunol 12(1):152-126.

Wu, J. et al. (Jun. 1999) "Hepetitis B Vaccination in High-Risk Infants: 10-year Follow-up," The Journal of Infectious Diseases 179(6):1319-1325.

Yero et al. (2007). "Identification by genomic immunization of a pool of DNA vaccine candidates that confer protective immunity in mice against Neisseria meningitidis serogroup B," Vaccine, 25(28):5175-88.

Zelnik, V. et al. (Mar. 2004) "An Enzyme-linked Immunosorbent Assay (ELISA) for Detection of Marek's Disease Virus-Specific Antibodies and its Application in an Experimental Vaccine Trial," Journal of Veterinary Medicine. B, Infectious Diseases and Veterinary Public Health 51(2):61-67.

* cited by examiner

SEQUENCE LISTING

<160> NUMBER OF SEQ ID NOS: 30

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT

<213> ORGANISM: Neisseria meningitidis

<400> SEQUENCE: 2

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245
```

<210> SEQ ID NO 3
<211> LENGTH: 250
<212> TYPE: PRT
<213> ORGANISM: Neisseria meningitidis

<400> SEQUENCE: 3

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
```

```
                        100                 105                 110
Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 644
<212> TYPE: PRT
<213> ORGANISM: Artificial Sequence
<220> FEATURE:
<223> OTHER INFORMATION: Hybrid meningococcal antigen

<400> SEQUENCE: 4

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
```

```
              210                 215                 220
Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
                260                 265                 270

Pro Thr Ser Phe Ala Arg Phe Arg Ser Ala Arg Ser Arg Arg Ser
            275                 280                 285

Leu Pro Ala Glu Met Pro Leu Ile Pro Val Asn Gln Ala Asp Thr Leu
            290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
                355                 360                 365

Phe His Thr Glu Asn Gly Arg Pro Ser Pro Ser Arg Gly Arg Phe Ala
            370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Glu Val Ala Gly Lys Tyr
            435                 440                 445

Ser Tyr Arg Pro Thr Asp Ala Glu Lys Gly Gly Phe Gly Val Phe Ala
            450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
            530                 535                 540

Ala Asp Ile Phe Asp Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640
```

Ala Ala Lys Gln

<210> SEQ ID NO 5
<211> LENGTH: 434
<212> TYPE: PRT
<213> ORGANISM: Artificial Sequence
<220> FEATURE:
<223> OTHER INFORMATION: Hybrid meningococcal antigen

<400> SEQUENCE: 5

Met Val Ser Ala Val Ile Gly Ser Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
            50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
            115                 120                 125

Ala Thr Arg Ala Arg Val Lys Ile Val Thr Tyr Gly Asn Val Thr Tyr
            130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

```
Ala Lys Gln Gly Asn Gly Lys Ile Glu His Leu Lys Ser Pro Glu Leu
            355                 360                 365

Asn Val Asp Leu Ala Ala Ala Asp Ile Lys Pro Asp Gly Lys Arg His
        370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Asp Val Glu Ala Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
            85                  90                  95

Thr Lys Leu Ala Asp Thr Asp Ala Ala Leu Ala Asp Thr Asp Ala Ala
        100                 105                 110

Leu Asp Ala Thr Thr Asn Ala Leu Asn Lys Leu Gly Glu Asn Ile Thr
    115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
        180                 185                 190

Asn Val Asp Ala Lys Val Lys Ala Ala Glu Thr Ala Ala Gly Lys Ala
    195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
        260                 265                 270

Glu Lys Leu Asp Thr Arg Leu Ala Ser Ala Glu Lys Ser Ile Ala Asp
    275                 280                 285
```

His Asp Thr Arg Leu Asn Gly Leu Asp Lys Thr Val Ser Asp Leu Arg
            290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 7
<211> LENGTH: 792
<212> TYPE: PRT
<213> ORGANISM: Neisseria meningitidis

<400> SEQUENCE: 7

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
                20                  25                  30

Pro Val Lys Ala Glu Ile Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Asn
210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
        275                 280                 285

Tyr Asn Leu Thr Ala Ser Trp Arg Glu Ala Asp Asp Val Asn Arg
290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
                325                 330                 335

-continued

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
            355                 360                 365

Asp Thr Arg Phe Lys Arg Phe Thr Leu Arg Leu Asp Ser His Pro Leu
        370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
                405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
        435                 440                 445

Ser Ser Arg Ala Gly Ile Arg Tyr Asp His Thr Lys Met Thr Pro Gln
    450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                485                 490                 495

Asn Gln Ala Trp Arg Val Gly Tyr Asp Ile Thr Ser Gly Tyr Arg Val
            500                 505                 510

Pro Asn Ala Ser Glu Val Tyr Phe Thr Tyr Asn His Gly Ser Gly Asn
        515                 520                 525

Trp Leu Pro Asn Pro Asn Leu Lys Ala Glu Arg Ser Thr Thr His Thr
    530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Gln Lys Leu Thr
                565                 570                 575

Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
        595                 600                 605

Asp Lys Ala Arg Ile Arg Gly Ile Glu Leu Thr Gly Arg Leu Asn Val
    610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
    690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
            755                 760                 765

Arg Asp Gly Lys Gly Leu Asp Arg Tyr Arg Ala Pro Gly Arg Asn Tyr
770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8

Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
                20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
        275                 280                 285

Tyr Asn Leu Leu Ala Ser Tyr Trp Arg Glu Ala Asp Val Asn Arg
290                 295                 300

Arg Arg Asn Thr Asn Leu Phe Tyr Glu Trp Thr Pro Glu Ser Asp Arg
305                 310                 315                 320

Leu Ser Met Val Lys Ala Asp Val Asp Tyr Gln Lys Thr Lys Val Ser
                325                 330                 335

```
Ala Val Asn Tyr Lys Gly Ser Phe Pro Ile Glu Asp Ser Ser Thr Leu
            340                 345                 350

Thr Arg Asn Tyr Asn Gln Lys Asp Leu Asp Glu Ile Tyr Asn Arg Ser
            355                 360                 365

Met Asp Thr Arg Phe Lys Arg Ile Thr Leu Arg Leu Asp Ser His Pro
    370                 375                 380

Leu Gln Leu Gly Gly Gly Arg His Arg Leu Ser Phe Lys Thr Phe Ala
385                 390                 395                 400

Ser Arg Arg Asp Phe Glu Asn Leu Asn Arg Asp Asp Tyr Tyr Phe Ser
                405                 410                 415

Gly Arg Val Val Arg Thr Thr Ser Ser Ile Gln His Pro Val Lys Thr
            420                 425                 430

Thr Asn Tyr Gly Phe Ser Leu Ser Asp Gln Ile Gln Trp Asn Asp Val
            435                 440                 445

Phe Ser Ser Arg Ala Gly Ile Arg Tyr Asp His Thr Lys Met Thr Pro
    450                 455                 460

Gln Glu Leu Asn Ala Glu Cys His Ala Cys Asp Lys Thr Pro Pro Ala
465                 470                 475                 480

Ala Asn Thr Tyr Lys Gly Trp Ser Gly Phe Val Gly Leu Ala Ala Gln
            485                 490                 495

Leu Asn Gln Ala Trp Arg Val Gly Tyr Asp Ile Thr Ser Gly Tyr Arg
                500                 505                 510

Val Pro Asn Ala Ser Glu Val Tyr Phe Thr Tyr Asn His Gly Ser Gly
            515                 520                 525

Asn Trp Leu Pro Asn Pro Asn Leu Lys Ala Glu Arg Thr Thr Thr His
    530                 535                 540

Thr Leu Ser Leu Gln Gly Arg Ser Glu Lys Gly Thr Leu Asp Ala Asn
545                 550                 555                 560

Leu Tyr Gln Ser Asn Tyr Arg Asn Phe Leu Ser Glu Glu Gln Lys Leu
                565                 570                 575

Thr Thr Ser Gly Asp Val Ser Cys Thr Gln Met Asn Tyr Tyr Tyr Gly
            580                 585                 590

Met Cys Ser Asn Pro Tyr Ser Glu Lys Leu Glu Trp Gln Met Gln Asn
    595                 600                 605

Ile Asp Lys Ala Arg Ile Arg Gly Ile Glu Leu Thr Gly Arg Leu Asn
    610                 615                 620

Val Asp Lys Val Ala Ser Phe Val Pro Glu Gly Trp Lys Leu Phe Gly
625                 630                 635                 640

Ser Leu Gly Tyr Ala Lys Ser Lys Leu Ser Gly Asp Asn Ser Leu Leu
                645                 650                 655

Ser Thr Gln Pro Leu Lys Val Ile Ala Gly Ile Asp Tyr Glu Ser Pro
            660                 665                 670

Ser Glu Lys Trp Gly Val Phe Ser Arg Leu Thr Tyr Leu Gly Ala Lys
            675                 680                 685

Lys Val Lys Asp Ala Gln Tyr Thr Val Tyr Glu Asn Lys Gly Trp Gly
            690                 695                 700

Thr Pro Leu Gln Lys Lys Val Lys Asp Tyr Pro Trp Leu Asn Lys Ser
705                 710                 715                 720

Ala Tyr Val Phe Asp Met Tyr Gly Phe Tyr Lys Pro Val Lys Asn Leu
                725                 730                 735

Thr Leu Arg Ala Gly Val Tyr Asn Val Phe Asn Arg Lys Tyr Thr Thr
            740                 745                 750
```

```
Trp Asp Ser Leu Arg Gly Leu Tyr Ser Tyr Ser Thr Asn Ser Val
        755                 760                 765

Asp Arg Asp Gly Lys Gly Leu Asp Arg Tyr Arg Ala Pro Ser Arg Asn
770                 775                 780

Tyr Ala Val Ser Leu Glu Trp Lys Phe
785                 790

<210> SEQ ID NO 9
<211> LENGTH: 488
<212> TYPE: PRT
<213> ORGANISM: Neisseria meningitidis

<400> SEQUENCE: 9

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335
```

-continued

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 10
<211> LENGTH: 364
<212> TYPE: PRT
<213> ORGANISM: Neisseria meningitidis

<400> SEQUENCE: 10

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60

Asp Gly Thr Ile Thr Gln Lys Asp Ala Thr Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys

```
                210                 215                 220
Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
                260                 265                 270

Ala Arg Ile Asp Ser Leu Asp Lys Asn Val Ala Asn Leu Arg Lys Glu
            275                 280                 285

Thr Arg Gln Gly Leu Ala Glu Gln Ala Ala Leu Ser Gly Leu Phe Gln
        290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
                340                 345                 350

Ser Ala Ala Tyr His Val Gly Val Asn Tyr Glu Trp
        355                 360

<210> SEQ ID NO 11
<211> LENGTH: 174
<212> TYPE: PRT
<213> ORGANISM: Neisseria meningitidis

<400> SEQUENCE: 11

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
        50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
                100                 105                 110

Asp Leu Gly Gly Ser Asp Ser Phe Ser Gln Thr Ser Ile Gly Leu Gly
            115                 120                 125

Val Leu Thr Gly Val Ser Tyr Ala Val Thr Pro Asn Val Asp Leu Asp
        130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 12
<211> LENGTH: 591
<212> TYPE: PRT
<213> ORGANISM: Neisseria meningitidis

<400> SEQUENCE: 12

Met Asn Lys Ile Tyr Arg Ile Ile Trp Asn Ser Ala Leu Asn Ala Trp
```

-continued

```
  1               5                   10                  15
Val Val Val Ser Glu Leu Thr Arg Asn His Thr Lys Arg Ala Ser Ala
              20                  25                  30
Thr Val Lys Thr Ala Val Leu Ala Thr Leu Leu Phe Ala Thr Val Gln
              35                  40                  45
Ala Ser Ala Asn Asn Glu Glu Gln Glu Glu Asp Leu Tyr Leu Asp Pro
 50                  55                  60
Val Gln Arg Thr Val Ala Val Leu Ile Val Asn Ser Asp Lys Glu Gly
 65                  70                  75                  80
Thr Gly Glu Lys Glu Lys Val Glu Glu Asn Ser Asp Trp Ala Val Tyr
                  85                  90                  95
Phe Asn Glu Lys Gly Val Leu Thr Ala Arg Glu Ile Thr Leu Lys Ala
                 100                 105                 110
Gly Asp Asn Leu Lys Ile Lys Gln Asn Gly Thr Asn Phe Thr Tyr Ser
                 115                 120                 125
Leu Lys Lys Asp Leu Thr Asp Leu Thr Ser Val Gly Thr Glu Lys Leu
 130                 135                 140
Ser Phe Ser Ala Asn Gly Asn Lys Val Asn Ile Thr Ser Asp Thr Lys
 145                 150                 155                 160
Gly Leu Asn Phe Ala Lys Glu Thr Ala Gly Thr Asn Gly Asp Thr Thr
                 165                 170                 175
Val His Leu Asn Gly Ile Gly Ser Thr Leu Thr Asp Thr Leu Leu Asn
                 180                 185                 190
Thr Gly Ala Thr Thr Asn Val Thr Asn Asp Asn Val Thr Asp Asp Glu
                 195                 200                 205
Lys Lys Arg Ala Ala Ser Val Lys Asp Val Leu Asn Ala Gly Trp Asn
 210                 215                 220
Ile Lys Gly Val Lys Pro Gly Thr Thr Ala Ser Asp Asn Val Asp Phe
 225                 230                 235                 240
Val Arg Thr Tyr Asp Thr Val Glu Phe Leu Ser Ala Asp Thr Lys Thr
                 245                 250                 255
Thr Thr Val Asn Val Glu Ser Lys Asp Asn Gly Lys Lys Thr Glu Val
                 260                 265                 270
Lys Ile Gly Ala Lys Thr Ser Val Ile Lys Glu Lys Asp Gly Lys Leu
                 275                 280                 285
Val Thr Gly Lys Asp Lys Gly Glu Asn Gly Ser Ser Thr Asp Glu Gly
                 290                 295                 300
Glu Gly Leu Val Thr Ala Lys Glu Val Ile Asp Ala Val Asn Lys Ala
 305                 310                 315                 320
Gly Trp Arg Met Lys Thr Thr Ala Asn Gly Gln Thr Gly Gln Ala
                 325                 330                 335
Asp Lys Phe Glu Thr Val Thr Ser Gly Thr Asn Val Thr Phe Ala Ser
                 340                 345                 350
Gly Lys Gly Thr Thr Ala Thr Val Ser Lys Asp Asp Gln Gly Asn Ile
                 355                 360                 365
Thr Val Met Tyr Asp Val Asn Val Gly Asp Ala Leu Asn Val Asn Gln
                 370                 375                 380
Leu Gln Asn Ser Gly Trp Asn Leu Asp Ser Lys Ala Val Ala Gly Ser
 385                 390                 395                 400
Ser Gly Lys Val Ile Ser Gly Asn Val Ser Pro Ser Lys Gly Lys Met
                 405                 410                 415
Asp Glu Thr Val Asn Ile Asn Ala Gly Asn Asn Ile Glu Ile Thr Arg
                 420                 425                 430
```

```
Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
    580                 585                 590

<210> SEQ ID NO 13
<211> LENGTH: 1457
<212> TYPE: PRT
<213> ORGANISM: Neisseria meningitidis

<400> SEQUENCE: 13

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
```

```
                210                 215                 220
Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640
```

-continued

Phe Phe Ser Gly Arg Pro Thr Pro His Ala Tyr Asn His Leu Asn Asp
            645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
            675                 680                 685

Gly Gly Gln Ala Val Val Ser Arg Asn Val Ala Lys Val Lys Gly Asp
            690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
            725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
            805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
            850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
            885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Ser Arg Ser Leu Leu
930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
            965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
            995                 1000                1005

Leu Glu Gln Leu Thr Val Val Glu Gly Lys Asp Asn Lys Pro Leu Ser
            1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
            1045                1050                1055

-continued

```
Pro Val Lys Glu Gln Glu Leu Ser Asp Lys Leu Gly Lys Ala Glu Ala
            1060                1065                1070
Lys Lys Gln Ala Glu Lys Asp Asn Ala Gln Ser Leu Asp Ala Leu Ile
        1075                1080                1085
Ala Ala Gly Arg Asp Ala Val Glu Lys Thr Glu Ser Val Ala Glu Pro
    1090                1095                1100
Ala Arg Gln Ala Gly Gly Glu Asn Val Gly Ile Met Gln Ala Glu Glu
1105                1110                1115                1120
Glu Lys Lys Arg Val Gln Ala Asp Lys Asp Thr Ala Leu Ala Lys Gln
                1125                1130                1135
Arg Glu Ala Glu Thr Arg Pro Ala Thr Thr Ala Phe Pro Arg Ala Arg
            1140                1145                1150
Arg Ala Arg Arg Asp Leu Pro Gln Leu Gln Pro Gln Pro Gln Pro Gln
        1155                1160                1165
Pro Gln Arg Asp Leu Ile Ser Arg Tyr Ala Asn Ser Gly Leu Ser Glu
    1170                1175                1180
Phe Ser Ala Thr Leu Asn Ser Val Phe Ala Val Gln Asp Glu Leu Asp
1185                1190                1195                1200
Arg Val Phe Ala Glu Asp Arg Arg Asn Ala Val Trp Thr Ser Gly Ile
            1205                1210                1215
Arg Asp Thr Lys His Tyr Arg Ser Gln Asp Phe Arg Ala Tyr Arg Gln
        1220                1225                1230
Gln Thr Asp Leu Arg Gln Ile Gly Met Gln Lys Asn Leu Gly Ser Gly
    1235                1240                1245
Arg Val Gly Ile Leu Phe Ser His Asn Arg Thr Glu Asn Thr Phe Asp
1250                1255                1260
Asp Gly Ile Gly Asn Ser Ala Arg Leu Ala His Gly Ala Val Phe Gly
1265                1270                1275                1280
Gln Tyr Gly Ile Asp Arg Phe Tyr Ile Gly Ile Ser Ala Gly Ala Gly
            1285                1290                1295
Phe Ser Ser Gly Ser Leu Ser Asp Gly Ile Gly Gly Lys Ile Arg Arg
        1300                1305                1310
Arg Val Leu His Tyr Gly Ile Gln Ala Arg Tyr Arg Ala Gly Phe Gly
    1315                1320                1325
Gly Phe Gly Ile Glu Pro His Ile Gly Ala Thr Arg Tyr Phe Val Gln
1330                1335                1340
Lys Ala Asp Tyr Arg Tyr Glu Asn Val Asn Ile Ala Thr Pro Gly Leu
1345                1350                1355                1360
Ala Phe Asn Arg Tyr Arg Ala Gly Ile Lys Ala Asp Tyr Ser Phe Lys
            1365                1370                1375
Pro Ala Gln His Ile Ser Ile Thr Pro Tyr Leu Ser Leu Ser Tyr Thr
        1380                1385                1390
Asp Ala Ala Ser Gly Lys Val Arg Thr Arg Val Asn Thr Ala Val Leu
    1395                1400                1405
Ala Gln Asp Phe Gly Lys Thr Arg Ser Ala Glu Trp Gly Val Asn Ala
1410                1415                1420
Glu Ile Lys Gly Phe Thr Leu Ser Leu His Ala Ala Ala Lys Gly
1425                1430                1435                1440
Pro Gln Leu Glu Ala Gln His Ser Ala Gly Ile Lys Leu Gly Tyr Arg
                1445                1450                1455
Trp

<210> SEQ ID NO 14
```

<211> LENGTH: 797
<212> TYPE: PRT
<213> ORGANISM: Neisseria meningitidis

<400> SEQUENCE: 14

```
Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
370                 375                 380

Ser Lys Glu Arg Val Glu Leu Leu Gly Tyr Phe Asp Asn Val Gln Phe
```

```
            385                 390                 395                 400
Asp Ala Val Pro Leu Ala Gly Thr Pro Asp Lys Val Asp Leu Asn Met
                    405                 410                 415

Ser Leu Thr Glu Arg Ser Thr Gly Ser Leu Asp Leu Ser Ala Gly Trp
                420                 425                 430

Val Gln Asp Thr Gly Leu Val Met Ser Ala Gly Val Ser Gln Asp Asn
            435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Ala Gly
                500                 505                 510

Ala Gly Ile Arg Met Ser Val Pro Val Thr Glu Tyr Asp Arg Val Asn
            515                 520                 525

Phe Gly Leu Val Ala Glu His Leu Thr Val Asn Thr Tyr Asn Lys Ala
        530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
    610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
        755                 760                 765

Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795

<210> SEQ ID NO 15
```

<211> LENGTH: 621
<212> TYPE: PRT
<213> ORGANISM: Neisseria meningitidis

<400> SEQUENCE: 15

```
Leu Leu Asp Asp Arg Gln Phe Gly Val Met Met Lys Asn Gly Tyr Ser
1               5                   10                  15

Thr Arg Asn Arg Glu Trp Thr Asn Thr Leu Gly Phe Gly Val Ser Asn
            20                  25                  30

Asp Arg Val Asp Ala Ala Leu Leu Tyr Ser Gln Arg Gly His Glu
        35                  40                  45

Thr Glu Ser Ala Gly Asn Arg Gly Tyr Ala Val Glu Gly Gly Ser
    50                  55                  60

Gly Ala Asn Ile Arg Gly Ser Ala Arg Gly Ile Pro Asp Ser Lys
65                  70                  75                  80

His Lys Tyr His Ser Phe Leu Gly Lys Ile Ala Tyr Gln Ile Asn Asp
                85                  90                  95

Asn His Arg Ile Gly Ala Ser Leu Asn Gly Gln Gln Gly His Asn Tyr
            100                 105                 110

Thr Val Glu Glu Ser Tyr Asn Leu Thr Ala Ser Ser Trp Arg Glu Ala
        115                 120                 125

Asp Asp Val Asn Arg Arg Asn Ala Asn Leu Phe Tyr Glu Trp Met
    130                 135                 140

Pro Asp Ser Asn Trp Leu Ser Ser Leu Lys Ala Asp Phe Asp Tyr Gln
145                 150                 155                 160

Lys Thr Lys Val Ala Ala Val Asn Asn Lys Gly Ser Phe Pro Met Asp
                165                 170                 175

Tyr Ser Thr Trp Thr Arg Asn Tyr Asn Gln Lys Asp Leu Asp Glu Ile
            180                 185                 190

Tyr Asn Arg Ser Met Asp Thr Arg Phe Lys Arg Phe Thr Leu Arg Leu
        195                 200                 205

Asp Ser His Pro Leu Gln Leu Gly Gly Gly Arg His Arg Leu Ser Phe
    210                 215                 220

Lys Thr Phe Val Ser Arg Arg Asp Phe Glu Asn Leu Asn Arg Asp Asp
225                 230                 235                 240

Tyr Tyr Phe Ser Gly Arg Val Val Arg Thr Thr Ser Ile Gln His
                245                 250                 255

Pro Val Lys Thr Thr Asn Tyr Gly Phe Ser Leu Ser Asp Gln Ile Gln
            260                 265                 270

Trp Asn Asp Val Phe Ser Ser Arg Ala Gly Ile Arg Tyr Asp His Thr
        275                 280                 285

Lys Met Thr Pro Gln Glu Leu Asn Ala Glu Cys His Ala Cys Asp Lys
    290                 295                 300

Thr Pro Pro Ala Ala Asn Thr Tyr Lys Gly Trp Ser Gly Phe Val Gly
305                 310                 315                 320

Leu Ala Ala Gln Leu Asn Gln Ala Trp His Val Gly Tyr Asp Ile Thr
                325                 330                 335

Ser Gly Tyr Arg Val Pro Asn Ala Ser Glu Val Tyr Phe Thr Tyr Asn
            340                 345                 350

His Gly Ser Gly Asn Trp Leu Pro Asn Pro Asn Leu Lys Ala Glu Arg
        355                 360                 365

Ser Thr Thr His Thr Leu Ser Leu Gln Gly Arg Ser Glu Lys Gly Met
    370                 375                 380

Leu Asp Ala Asn Leu Tyr Gln Ser Asn Tyr Arg Asn Phe Leu Ser Glu
```

```
                385                 390                 395                 400
Glu Gln Lys Leu Thr Thr Ser Gly Thr Pro Gly Cys Thr Glu Asn
                405                 410                 415

Ala Tyr Tyr Gly Ile Cys Ser Asp Pro Tyr Lys Glu Lys Leu Asp Trp
                420                 425                 430

Gln Met Lys Asn Ile Asp Lys Ala Arg Ile Arg Gly Ile Glu Leu Thr
                435                 440                 445

Gly Arg Leu Asn Val Asp Lys Val Ala Ser Phe Val Pro Glu Gly Trp
    450                 455                 460

Lys Leu Phe Gly Ser Leu Gly Tyr Ala Lys Ser Lys Leu Ser Gly Asp
465                 470                 475                 480

Asn Ser Leu Leu Ser Thr Gln Pro Leu Lys Val Ile Ala Gly Ile Asp
                485                 490                 495

Tyr Glu Ser Pro Ser Glu Lys Trp Gly Val Phe Ser Arg Leu Thr Tyr
                500                 505                 510

Leu Gly Ala Lys Lys Ala Lys Asp Ala Gln Tyr Thr Val Tyr Glu Asn
                515                 520                 525

Lys Gly Trp Gly Thr Pro Leu Gln Lys Val Lys Asp Tyr Pro Trp
    530                 535                 540

Leu Asn Lys Ser Ala Tyr Val Phe Asp Met Tyr Gly Phe Tyr Lys Pro
545                 550                 555                 560

Ala Lys Asn Leu Thr Leu Arg Ala Gly Val Tyr Asn Val Phe Asn Arg
                565                 570                 575

Lys Tyr Thr Thr Trp Asp Ser Leu Arg Gly Leu Tyr Ser Tyr Ser Thr
                580                 585                 590

Thr Asn Ser Val Asp Arg Asp Gly Lys Gly Leu Asp Arg Tyr Arg Ala
                595                 600                 605

Pro Ser Arg Asn Tyr Ala Val Ser Leu Glu Trp Lys Phe
    610                 615                 620

<210> SEQ ID NO 16
<211> LENGTH: 768
<212> TYPE: PRT
<213> ORGANISM: Neisseria meningitidis

<400> SEQUENCE: 16

Ala Asp Glu Ala Ala Thr Glu Thr Thr Pro Val Lys Ala Glu Ile Lys
1               5                   10                  15

Ala Val Arg Val Lys Gly Gln Arg Asn Ala Pro Ala Ala Val Glu Arg
                20                  25                  30

Val Asn Leu Asn Arg Ile Lys Gln Glu Met Ile Arg Asp Asn Lys Asp
            35                  40                  45

Leu Val Arg Tyr Ser Thr Asp Val Gly Leu Ser Asp Ser Gly Arg His
    50                  55                  60

Gln Lys Gly Phe Ala Val Arg Gly Val Glu Gly Asn Arg Val Gly Val
65                  70                  75                  80

Ser Ile Asp Gly Val Asn Leu Pro Asp Ser Glu Glu Asn Ser Leu Tyr
                85                  90                  95

Ala Arg Tyr Gly Asn Phe Asn Ser Ser Arg Leu Ser Ile Asp Pro Glu
                100                 105                 110

Leu Val Arg Asn Ile Glu Ile Val Lys Gly Ala Asp Ser Phe Asn Thr
            115                 120                 125

Gly Ser Gly Ala Leu Gly Gly Val Asn Tyr Gln Thr Leu Gln Gly
    130                 135                 140
```

```
Arg Asp Leu Leu Leu Asp Arg Gln Phe Gly Val Met Met Lys Asn
145                 150                 155                 160

Gly Tyr Ser Thr Arg Asn Arg Glu Trp Thr Asn Thr Leu Gly Phe Gly
                165                 170                 175

Val Ser Asn Asp Arg Val Asp Ala Ala Leu Leu Tyr Ser Gln Arg Arg
            180                 185                 190

Gly His Glu Thr Glu Ser Ala Gly Asn Arg Gly Tyr Ala Val Glu Gly
        195                 200                 205

Glu Gly Ser Gly Ala Asn Ile Arg Gly Ser Ala Arg Gly Ile Pro Asp
    210                 215                 220

Ser Ser Lys His Lys Tyr His Ser Phe Leu Gly Lys Ile Ala Tyr Gln
225                 230                 235                 240

Ile Asn Asp Asn His Arg Ile Gly Ala Ser Leu Asn Gly Gln Gln Gly
                245                 250                 255

His Asn Tyr Thr Val Glu Glu Ser Tyr Asn Leu Thr Ala Ser Ser Trp
            260                 265                 270

Arg Glu Ala Asp Asp Val Asn Arg Arg Asn Ala Asn Leu Phe Tyr
        275                 280                 285

Glu Trp Met Pro Asp Ser Asn Trp Leu Ser Ser Leu Lys Ala Asp Phe
290                 295                 300

Asp Tyr Gln Lys Thr Lys Val Ala Ala Val Asn Asn Lys Gly Ser Phe
305                 310                 315                 320

Pro Met Asp Tyr Ser Thr Trp Thr Arg Asn Tyr Asn Gln Lys Asp Leu
                325                 330                 335

Asp Glu Ile Tyr Asn Arg Ser Met Asp Thr Arg Phe Lys Arg Phe Thr
            340                 345                 350

Leu Arg Leu Asp Ser His Pro Leu Gln Leu Gly Gly Gly Arg His Arg
        355                 360                 365

Leu Ser Phe Lys Thr Phe Val Ser Arg Arg Asp Phe Glu Asn Leu Asn
370                 375                 380

Arg Asp Asp Tyr Tyr Phe Ser Gly Arg Val Val Arg Thr Thr Ser Ser
385                 390                 395                 400

Ile Gln His Pro Val Lys Thr Thr Asn Tyr Gly Phe Ser Leu Ser Asp
                405                 410                 415

Gln Ile Gln Trp Asn Asp Val Phe Ser Ser Arg Ala Gly Ile Arg Tyr
            420                 425                 430

Asp His Thr Lys Met Thr Pro Gln Glu Leu Asn Ala Glu Cys His Ala
        435                 440                 445

Cys Asp Lys Thr Pro Pro Ala Ala Asn Thr Tyr Lys Gly Trp Ser Gly
450                 455                 460

Phe Val Gly Leu Ala Ala Gln Leu Asn Gln Ala Trp His Val Gly Tyr
465                 470                 475                 480

Asp Ile Thr Ser Gly Tyr Arg Val Pro Asn Ala Ser Glu Val Tyr Phe
                485                 490                 495

Thr Tyr Asn His Gly Ser Gly Asn Trp Leu Pro Asn Pro Asn Leu Lys
            500                 505                 510

Ala Glu Arg Ser Thr Thr His Thr Leu Ser Leu Gln Gly Arg Ser Glu
        515                 520                 525

Lys Gly Met Leu Asp Ala Asn Leu Tyr Gln Ser Asn Tyr Arg Asn Phe
530                 535                 540

Leu Ser Glu Glu Gln Lys Leu Thr Thr Ser Gly Thr Pro Gly Cys Thr
545                 550                 555                 560

Glu Glu Asn Ala Tyr Tyr Gly Ile Cys Ser Asp Pro Tyr Lys Glu Lys
```

```
                          565                 570                 575
Leu Asp Trp Gln Met Lys Asn Ile Asp Lys Ala Arg Ile Arg Gly Ile
                580                 585                 590

Glu Leu Thr Gly Arg Leu Asn Val Asp Lys Val Ala Ser Phe Val Pro
            595                 600                 605

Glu Gly Trp Lys Leu Phe Gly Ser Leu Gly Tyr Ala Lys Ser Lys Leu
        610                 615                 620

Ser Gly Asp Asn Ser Leu Leu Ser Thr Gln Pro Leu Lys Val Ile Ala
625                 630                 635                 640

Gly Ile Asp Tyr Glu Ser Pro Ser Glu Lys Trp Gly Val Phe Ser Arg
                645                 650                 655

Leu Thr Tyr Leu Gly Ala Lys Lys Ala Lys Asp Ala Gln Tyr Thr Val
                660                 665                 670

Tyr Glu Asn Lys Gly Trp Gly Thr Pro Leu Gln Lys Lys Val Lys Asp
            675                 680                 685

Tyr Pro Trp Leu Asn Lys Ser Ala Tyr Val Phe Asp Met Tyr Gly Phe
        690                 695                 700

Tyr Lys Pro Ala Lys Asn Leu Thr Leu Arg Ala Gly Val Tyr Asn Val
705                 710                 715                 720

Phe Asn Arg Lys Tyr Thr Thr Trp Asp Ser Leu Arg Gly Leu Tyr Ser
                725                 730                 735

Tyr Ser Thr Asn Ser Val Asp Arg Asp Gly Lys Gly Leu Asp Arg
                740                 745                 750

Tyr Arg Ala Pro Ser Arg Asn Tyr Ala Val Ser Leu Glu Trp Lys Phe
            755                 760                 765

<210> SEQ ID NO 17
<211> LENGTH: 915
<212> TYPE: PRT
<213> ORGANISM: Neisseria meningitidis

<400> SEQUENCE: 17

Met Gln Gln Gln His Leu Phe Arg Phe Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175
```

-continued

```
Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Asn Tyr Ala
                245                 250                 255

Tyr Phe Ile Val Lys Glu Glu Cys Lys Asn Gly Ser Tyr Glu Thr Cys
            260                 265                 270

Lys Ala Asn Pro Lys Lys Asp Val Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Lys Lys Gln Ala Gly Ser Leu Pro Gly Asn Gly
        355                 360                 365

Lys Tyr Ala Gly Asn His Lys Tyr Gly Gly Leu Phe Thr Asn Gly Glu
    370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Gly Ser Asn Leu Arg His
            500                 505                 510

Gln Asp Tyr Tyr Tyr Gln His Ala Asn Arg Ala Tyr Ser Ser Asn Thr
        515                 520                 525

Pro Pro Gln Asn Asn Gly Lys Lys Ile Ser Pro Asn Gly Ser Glu Thr
    530                 535                 540

Ser Pro Tyr Trp Val Thr Ile Gly Arg Gly Asn Val Val Thr Gly Gln
545                 550                 555                 560

Ile Cys Arg Leu Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
            580                 585                 590

Gly Arg Trp Ala Asp Val Gly Ala Gly Leu Arg Tyr Asp Tyr Arg Ser
```

```
                    595                 600                 605
Thr His Ser Asp Asp Gly Ser Val Ser Thr Gly Thr His Arg Thr Leu
        610                 615                 620

Ser Trp Asn Ala Gly Ile Val Leu Lys Pro Thr Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ala Gly Val Gln Ser Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700

Val Arg Gly Tyr Glu Ala Gln Ile Lys Asp Gly Lys Glu Ala Lys
705                 710                 715                 720

Gly Asp Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
    770                 775                 780

Ala Ile Gln Pro Ser Arg Tyr Val Val Gly Leu Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ala Arg Arg Thr Arg Pro Trp Tyr Ile Val
        835                 840                 845

Asp Val Ser Gly Tyr Tyr Thr Val Lys Lys His Phe Thr Leu Arg Ala
    850                 855                 860

Gly Val Tyr Asn Leu Leu Asn Tyr Arg Tyr Val Thr Trp Glu Asn Val
865                 870                 875                 880

Arg Gln Thr Ala Gly Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
            900                 905                 910

Met Lys Phe
        915

<210> SEQ ID NO 18
<211> LENGTH: 712
<212> TYPE: PRT
<213> ORGANISM: Neisseria meningitidis

<400> SEQUENCE: 18

Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Asp Thr Glu Ala Pro Arg Pro Ala Pro Lys Tyr Gln Asp Val Phe
        35                  40                  45
```

```
Ser Glu Lys Pro Gln Ala Gln Lys Asp Gln Gly Gly Tyr Gly Phe Ala
    50                  55                  60
Met Arg Leu Lys Arg Arg Asn Trp Tyr Pro Gln Ala Lys Glu Asp Glu
 65                  70                  75                  80
Val Lys Leu Asp Glu Ser Asp Trp Glu Ala Thr Gly Leu Pro Asp Glu
                 85                  90                  95
Pro Lys Glu Leu Pro Lys Arg Gln Lys Ser Val Ile Glu Lys Val Glu
                100                 105                 110
Thr Asp Ser Asp Asn Asn Ile Tyr Ser Ser Pro Tyr Leu Lys Pro Ser
            115                 120                 125
Asn His Gln Asn Gly Asn Thr Gly Asn Gly Ile Asn Gln Pro Lys Asn
        130                 135                 140
Gln Ala Lys Asp Tyr Glu Asn Phe Lys Tyr Val Tyr Ser Gly Trp Phe
145                 150                 155                 160
Tyr Lys His Ala Lys Arg Glu Phe Asn Leu Lys Val Glu Pro Lys Ser
                165                 170                 175
Ala Lys Asn Gly Asp Asp Gly Tyr Ile Phe Tyr His Gly Lys Glu Pro
            180                 185                 190
Ser Arg Gln Leu Pro Ala Ser Gly Lys Ile Thr Tyr Lys Gly Val Trp
        195                 200                 205
His Phe Ala Thr Asp Thr Lys Lys Gly Gln Lys Phe Arg Glu Ile Ile
210                 215                 220
Gln Pro Ser Lys Ser Gln Gly Asp Arg Tyr Ser Gly Phe Ser Gly Asp
225                 230                 235                 240
Asp Gly Glu Glu Tyr Ser Asn Lys Asn Lys Ser Thr Leu Thr Asp Gly
                245                 250                 255
Gln Glu Gly Tyr Gly Phe Thr Ser Asn Leu Glu Val Asp Phe His Asn
            260                 265                 270
Lys Lys Leu Thr Gly Lys Leu Ile Arg Asn Asn Ala Asn Thr Asp Asn
        275                 280                 285
Asn Gln Ala Thr Thr Thr Gln Tyr Tyr Ser Leu Glu Ala Gln Val Thr
290                 295                 300
Gly Asn Arg Phe Asn Gly Lys Ala Thr Ala Thr Asp Lys Pro Gln Gln
305                 310                 315                 320
Asn Ser Glu Thr Lys Glu His Pro Phe Val Ser Asp Ser Ser Leu
                325                 330                 335
Ser Gly Gly Phe Phe Gly Pro Gln Gly Glu Leu Gly Phe Arg Phe
            340                 345                 350
Leu Ser Asp Asp Gln Lys Val Ala Val Val Gly Ser Ala Lys Thr Lys
        355                 360                 365
Asp Lys Pro Ala Asn Gly Asn Thr Ala Ala Ser Gly Gly Thr Asp
370                 375                 380
Ala Ala Ala Ser Asn Gly Ala Ala Gly Thr Ser Ser Glu Asn Gly Lys
385                 390                 395                 400
Leu Thr Thr Val Leu Asp Ala Val Glu Leu Lys Leu Gly Asp Lys Glu
                405                 410                 415
Val Gln Lys Leu Asp Asn Phe Ser Asn Ala Ala Gln Leu Val Val Asp
            420                 425                 430
Gly Ile Met Ile Pro Leu Leu Pro Glu Ala Ser Glu Ser Gly Asn Asn
        435                 440                 445
Gln Ala Asn Gln Gly Thr Asn Gly Gly Thr Ala Phe Thr Arg Lys Phe
450                 455                 460
Asp His Thr Pro Glu Ser Asp Lys Lys Asp Ala Gln Ala Gly Thr Gln
```

```
            465                 470                 475                 480
        Thr Asn Gly Ala Gln Thr Ala Ser Asn Thr Ala Gly Asp Thr Asn Gly
                        485                 490                 495
        Lys Thr Lys Thr Tyr Glu Val Glu Val Cys Cys Ser Asn Leu Asn Tyr
                    500                 505                 510
        Leu Lys Tyr Gly Met Leu Thr Arg Lys Asn Ser Lys Ser Ala Met Gln
                    515                 520                 525
        Ala Gly Glu Ser Ser Ser Gln Ala Asp Ala Lys Thr Glu Gln Val Glu
                    530                 535                 540
        Gln Ser Met Phe Leu Gln Gly Glu Arg Thr Asp Glu Lys Glu Ile Pro
        545                 550                 555                 560
        Ser Glu Gln Asn Ile Val Tyr Arg Gly Ser Trp Tyr Gly Tyr Ile Ala
                        565                 570                 575
        Asn Asp Lys Ser Thr Ser Trp Ser Gly Asn Ala Ser Asn Ala Thr Ser
                    580                 585                 590
        Gly Asn Arg Ala Glu Phe Thr Val Asn Phe Ala Asp Lys Lys Ile Thr
                    595                 600                 605
        Gly Thr Leu Thr Ala Asp Asn Arg Gln Glu Ala Thr Phe Thr Ile Asp
                    610                 615                 620
        Gly Asn Ile Lys Asp Asn Gly Phe Glu Gly Thr Ala Lys Thr Ala Glu
        625                 630                 635                 640
        Ser Gly Phe Asp Leu Asp Gln Ser Asn Thr Thr Arg Thr Pro Lys Ala
                        645                 650                 655
        Tyr Ile Thr Asp Ala Lys Val Gln Gly Gly Phe Tyr Gly Pro Lys Ala
                    660                 665                 670
        Glu Glu Leu Gly Gly Trp Phe Ala Tyr Pro Gly Asp Lys Gln Thr Lys
                    675                 680                 685
        Asn Ala Thr Asn Ala Ser Gly Asn Ser Ser Ala Thr Val Val Phe Gly
                    690                 695                 700
        Ala Lys Arg Gln Gln Pro Val Arg
        705                 710

<210> SEQ ID NO 19
<211> LENGTH: 791
<212> TYPE: PRT
<213> ORGANISM: Neisseria meningitidis

<400> SEQUENCE: 19

Met Lys Pro Leu Gln Met Leu Pro Ile Ala Ala Leu Val Gly Ser Ile
        1               5                   10                  15
        Phe Gly Asn Pro Val Leu Ala Ala Asp Glu Ala Ala Thr Glu Thr Thr
                        20                  25                  30
        Pro Val Lys Ala Glu Ile Lys Ala Val Arg Val Lys Gly Gln Arg Asn
                    35                  40                  45
        Ala Pro Ala Ala Val Glu Arg Val Asn Leu Asn Arg Ile Lys Gln Glu
                    50                  55                  60
        Met Ile Arg Asp Asn Lys Asp Leu Val Arg Tyr Ser Thr Asp Val Gly
        65                  70                  75                  80
        Leu Ser Asp Ser Gly Arg His Gln Lys Gly Phe Ala Val Arg Gly Val
                        85                  90                  95
        Glu Gly Asn Arg Val Gly Val Ser Ile Asp Gly Val Asn Leu Pro Asp
                    100                 105                 110
        Ser Glu Glu Asn Ser Leu Tyr Ala Arg Tyr Gly Asn Phe Asn Ser Ser
                    115                 120                 125
```

-continued

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Asp Arg Gln
                165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
                195                 200                 205

Leu Leu Tyr Ser Gln Arg Arg Gly His Glu Thr Glu Ser Ala Gly Asn
    210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr His Ser Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
    275                 280                 285

Asn Leu Thr Ala Ser Ser Trp Arg Glu Ala Asp Asp Val Asn Arg Arg
290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Val Asn Asn Lys Gly Ser Phe Pro Met Asp Tyr Ser Thr Trp Thr Arg
                340                 345                 350

Asn Tyr Asn Gln Lys Asp Leu Asp Glu Ile Tyr Asn Arg Ser Met Asp
                355                 360                 365

Thr Arg Phe Lys Arg Phe Thr Leu Arg Leu Asp Ser His Pro Leu Gln
    370                 375                 380

Leu Gly Gly Gly Arg His Arg Leu Ser Phe Lys Thr Phe Val Ser Arg
385                 390                 395                 400

Arg Asp Phe Glu Asn Leu Asn Arg Asp Tyr Tyr Phe Ser Gly Arg
                405                 410                 415

Val Val Arg Thr Thr Ser Ser Ile Gln His Pro Val Lys Thr Thr Asn
                420                 425                 430

Tyr Gly Phe Ser Leu Ser Asp Gln Ile Gln Trp Asn Asp Val Phe Ser
    435                 440                 445

Ser Arg Ala Gly Ile Arg Tyr Asp His Thr Lys Met Thr Pro Gln Glu
450                 455                 460

Leu Asn Ala Glu Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Asn
                485                 490                 495

Gln Ala Trp His Val Gly Tyr Asp Ile Thr Ser Gly Tyr Arg Val Pro
                500                 505                 510

Asn Ala Ser Glu Val Tyr Phe Thr Tyr Asn His Gly Ser Gly Asn Trp
    515                 520                 525

Leu Pro Asn Pro Asn Leu Lys Ala Glu Arg Ser Thr Thr His Thr Leu
530                 535                 540

Ser Leu Gln Gly Arg Ser Glu Lys Gly Met Leu Asp Ala Asn Leu Tyr

```
            545                 550                 555                 560
        Gln Ser Asn Tyr Arg Asn Phe Leu Ser Glu Glu Gln Lys Leu Thr Thr
                            565                 570                 575

Ser Gly Thr Pro Gly Cys Thr Glu Glu Asn Ala Tyr Tyr Gly Ile Cys
                        580                 585                 590

Ser Asp Pro Tyr Lys Glu Lys Leu Asp Trp Gln Met Lys Asn Ile Asp
                        595                 600                 605

Lys Ala Arg Ile Arg Gly Ile Glu Leu Thr Gly Arg Leu Asn Val Asp
                        610                 615                 620

Lys Val Ala Ser Phe Val Pro Glu Gly Trp Lys Leu Phe Gly Ser Leu
        625                 630                 635                 640

Gly Tyr Ala Lys Ser Lys Leu Ser Gly Asp Asn Ser Leu Leu Ser Thr
                            645                 650                 655

Gln Pro Leu Lys Val Ile Ala Gly Ile Asp Tyr Glu Ser Pro Ser Glu
                        660                 665                 670

Lys Trp Gly Val Phe Ser Arg Leu Thr Tyr Leu Gly Ala Lys Lys Ala
                        675                 680                 685

Lys Asp Ala Gln Tyr Thr Val Tyr Glu Asn Lys Gly Trp Gly Thr Pro
                        690                 695                 700

Leu Gln Lys Lys Val Lys Asp Tyr Pro Trp Leu Asn Lys Ser Ala Tyr
        705                 710                 715                 720

Val Phe Asp Met Tyr Gly Phe Tyr Lys Pro Ala Lys Asn Leu Thr Leu
                            725                 730                 735

Arg Ala Gly Val Tyr Asn Val Phe Asn Arg Lys Tyr Thr Thr Trp Asp
                        740                 745                 750

Ser Leu Arg Gly Leu Tyr Ser Tyr Ser Thr Thr Asn Ser Val Asp Arg
                        755                 760                 765

Asp Gly Lys Gly Leu Asp Arg Tyr Arg Ala Pro Ser Arg Asn Tyr Ala
                        770                 775                 780

Val Ser Leu Glu Trp Lys Phe
        785                 790

<210> SEQ ID NO 20
<211> LENGTH: 186
<212> TYPE: PRT
<213> ORGANISM: Neisseria meningitidis

<400> SEQUENCE: 20

Met Asn Met Lys Thr Leu Leu Ala Leu Ala Val Ser Ala Val Cys Ser
        1               5                   10                  15

Val Gly Val Ala Gln Ala His Glu His Asn Thr Ile Pro Lys Gly Ala
                        20                  25                  30

Ser Ile Glu Val Lys Val Gln Gln Leu Asp Pro Val Asn Gly Asn Lys
                    35                  40                  45

Asp Val Gly Thr Val Thr Ile Thr Glu Ser Asn Tyr Gly Leu Val Phe
                50                  55                  60

Thr Pro Asp Leu Gln Gly Leu Ser Glu Gly Leu His Gly Phe His Ile
        65                  70                  75                  80

His Glu Asn Pro Ser Cys Glu Pro Lys Glu Lys Glu Gly Lys Leu Thr
                            85                  90                  95

Ala Gly Leu Gly Ala Gly Gly His Trp Asp Pro Lys Gly Ala Lys Gln
                        100                 105                 110

His Gly Tyr Pro Trp Gln Asp Asp Ala His Leu Gly Asp Leu Pro Ala
                        115                 120                 125
```

Leu Thr Val Leu His Asp Gly Thr Ala Thr Asn Pro Val Leu Ala Pro
         130                 135                 140

Arg Leu Lys His Leu Asp Asp Val Arg Gly His Ser Ile Met Ile His
145                 150                 155                 160

Thr Gly Gly Asp Asn His Ser Asp His Pro Ala Pro Leu Gly Gly Gly
                165                 170                 175

Gly Pro Arg Met Ala Cys Gly Val Ile Lys
            180                 185

<210> SEQ ID NO 21
<211> LENGTH: 116
<212> TYPE: PRT
<213> ORGANISM: Mus musculus

<400> SEQUENCE: 21

Asp Ile Val Leu Thr Gln Ser Pro Ser Ser Ile Tyr Ala Ser Leu Gly
1               5                   10                  15

Glu Arg Val Thr Leu Thr Cys Lys Ala Ser Gln Asp Ile His Asn Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Ser Ser Leu Glu Phe
65                  70                  75                  80

Glu Asp Ile Gly Ile Tyr Tyr Cys Leu Gln Tyr Asp Glu Phe Pro Pro
                85                  90                  95

Thr Phe Gly Gly Gly Thr Arg Leu Glu Ile Lys Arg Ala Asp Ala Ala
            100                 105                 110

Pro Thr Val Ser
        115

<210> SEQ ID NO 22
<211> LENGTH: 118
<212> TYPE: PRT
<213> ORGANISM: Mus musculus

<400> SEQUENCE: 22

Gln Val Gln Leu Gln Glu Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Asn Met Ser Trp Val Lys Gln Ser Asn Gly Lys Ser Leu Glu Trp Ile
        35                  40                  45

Gly Ile Ile Asp Pro Lys Tyr Gly Thr Ile Asn Tyr Asn Gln Lys Phe
    50                  55                  60

Lys Gly Lys Ala Thr Leu Thr Val Asp Gln Ala Ser Ser Thr Ala Tyr
65                  70                  75                  80

Met Gln Leu Asn Ser Leu Thr Ser Glu Asp Ser Ala Val Tyr Tyr Cys
                85                  90                  95

Val Arg Asp Tyr Tyr Gly Ser Ser Tyr Phe Asp Tyr Trp Gly Gln Gly
            100                 105                 110

Thr Thr Leu Thr Val Ser
            115

<210> SEQ ID NO 23
<211> LENGTH: 116

```
<212> TYPE: PRT
<213> ORGANISM: Mus musculus

<400> SEQUENCE: 23

Asp Ile Val Leu Thr Gln Thr Pro Ser Ser Ile Tyr Ala Ser Leu Gly
1               5                   10                  15

Glu Arg Val Thr Leu Thr Cys Lys Ala Ser Gln Asp Ile His Asn Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Gly Gly Ser Gly Gln Asp Tyr Ser Leu Thr Ile Ser Ser Leu Glu Phe
65                  70                  75                  80

Glu Asp Ile Gly Ile Tyr Tyr Cys Leu Gln Tyr Asp Glu Phe Pro Pro
                85                  90                  95

Thr Phe Gly Gly Gly Thr Arg Leu Glu Ile Lys Arg Ala Asp Ala Ala
            100                 105                 110

Pro Thr Val Ser
            115

<210> SEQ ID NO 24
<211> LENGTH: 118
<212> TYPE: PRT
<213> ORGANISM: Mus musculus

<400> SEQUENCE: 24

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Asn Met Ser Trp Val Lys Gln Ser Asn Gly Lys Ser Leu Glu Trp Ile
        35                  40                  45

Gly Ile Ile Asp Pro Lys Tyr Gly Thr Ile Asn Tyr Asn Gln Lys Phe
50                  55                  60

Lys Gly Lys Ala Thr Leu Thr Val Asp Gln Ala Ser Ser Thr Ala Tyr
65                  70                  75                  80

Met Gln Leu Asn Ser Leu Thr Ser Glu Asp Ser Ala Val Tyr Tyr Cys
                85                  90                  95

Val Arg Asp Tyr Tyr Gly Ser Ser Tyr Phe Asp Tyr Trp Gly Gln Gly
            100                 105                 110

Thr Thr Leu Thr Val Ser
            115

<210> SEQ ID NO 25
<211> LENGTH: 116
<212> TYPE: PRT
<213> ORGANISM: Mus musculus

<400> SEQUENCE: 25

Asp Ile Val Met Thr Gln Ser Gln Lys Phe Met Ser Thr Ser Val Gly
1               5                   10                  15

Asp Arg Val Ser Ile Thr Cys Lys Ala Ser Gln His Val Arg Thr Ala
            20                  25                  30

Val Ala Trp Tyr Gln Gln Lys Pro Gly Gln Ser Pro Lys Gly Leu Ile
        35                  40                  45

Tyr Leu Ala Ser Asn Arg Arg Thr Gly Val Pro Asp Arg Phe Thr Ala
```

```
                    50                  55                  60
Ser Gly Ser Gly Thr Asp Phe Thr Leu Thr Ile Thr Asn Val Gln Ser
 65                  70                  75                  80

Glu Asp Leu Ala Asp Tyr Phe Cys Leu Gln His Trp Asn Tyr Pro Phe
                 85                  90                  95

Thr Phe Gly Ser Gly Thr Lys Leu Glu Ile Lys Arg Ala Asp Ala Ala
            100                 105                 110

Pro Thr Val Ser
        115

<210> SEQ ID NO 26
<211> LENGTH: 118
<212> TYPE: PRT
<213> ORGANISM: Mus musculus

<400> SEQUENCE: 26

Glu Val Gln Leu Glu Glu Ser Gly Pro Glu Leu Val Lys Pro Gly Ala
 1               5                  10                  15

Ser Val Lys Ile Ser Cys Lys Ala Ser Gly Tyr Ser Phe Ser Asp Tyr
             20                  25                  30

Asn Met Ser Trp Val Lys Gln Ser Asn Gly Lys Ser Leu Glu Trp Ile
         35                  40                  45

Gly Ile Ile Asp Pro Lys Tyr Gly Thr Ile Asn Tyr Asn Gln Lys Phe
 50                  55                  60

Lys Gly Lys Ala Thr Leu Thr Val Asp Gln Ala Ser Ser Thr Ala Tyr
 65                  70                  75                  80

Met Gln Leu Asn Ser Leu Thr Ser Glu Asp Ser Ala Val Tyr Tyr Cys
                 85                  90                  95

Val Arg Asp Tyr Tyr Gly Ser Ser Tyr Phe Asp Tyr Trp Gly Gln Gly
            100                 105                 110

Thr Thr Leu Thr Val Ser
        115

<210> SEQ ID NO 27
<211> LENGTH: 114
<212> TYPE: PRT
<213> ORGANISM: Mus musculus

<400> SEQUENCE: 27

Asp Ile Val Leu Thr Gln Ser Pro Ser Ser Leu Thr Val Thr Ala Gly
 1               5                  10                  15

Glu Lys Val Thr Met Ser Cys Arg Ser Ser Gln Ser Leu Leu Asn Ser
             20                  25                  30

Gly Asn Gln Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Ile Tyr Tyr Cys Gln Asn
                 85                  90                  95

Asp Tyr Asn Tyr Pro Leu Thr Phe Gly Ala Gly Thr Lys Leu Glu Leu
            100                 105                 110

Lys Arg

<210> SEQ ID NO 28
```

```
<211> LENGTH: 124
<212> TYPE: PRT
<213> ORGANISM: Mus musculus

<400> SEQUENCE: 28

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Thr Tyr
            20                  25                  30

Tyr Trp Met Asn Trp Val Lys Gln Arg Pro Gly Gln Gly Leu Glu Trp
        35                  40                  45

Ile Gly Met Ile His Pro Asn Ser Gly Ser Thr Asn Tyr Asn Glu Lys
50                  55                  60

Phe Lys Asn Lys Ala Thr Leu Thr Val Asp Lys Ser Ser Ser Thr Ala
65                  70                  75                  80

Tyr Ile Gln Leu Ser Ser Leu Thr Ser Glu Asp Ser Ala Val Phe Tyr
                85                  90                  95

Cys Ala Ala His Tyr Asn Lys Tyr Glu Gly Tyr Phe Tyr Ala Met Asp
            100                 105                 110

Tyr Trp Gly Gln Gly Thr Ser Val Thr Val Ser Ser
        115                 120

<210> SEQ ID NO 29
<211> LENGTH: 261
<212> TYPE: PRT
<213> ORGANISM: Neisseria meningitidis

<400> SEQUENCE: 29

Cys Ser Ser Gly Ser Gly Ser Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
210                 215                 220
```

```
-continued

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 30
<211> LENGTH: 260
<212> TYPE: PRT
<213> ORGANISM: Neisseria meningitidis

<400> SEQUENCE: 30

Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260
```

IN VITRO POTENCY ASSAY FOR PROTEIN-BASED MENINGOCOCCAL VACCINES

CROSS REFERENCE TO RELATED APPLICATIONS

This application is the US National Phase of International Application No. PCT/EP2013/054670, filed Mar. 8, 2013 and published in English, which claims the benefit of US Provisional Patent Application No. 61/608,293 filed Mar. 8, 2012), the complete contents of which are hereby incorporated herein by reference for all purposes.

SUBMISSION OF SEQUENCE LISTING ON ASCII TEXT FILE

The content of the following submission on ASCII text file is incorporated herein by reference in entirety: a computer readable form (CRF) of the Sequence. Listing (file name: 303822004000SeqListing.txt, date recorded: Jun. 21, 2016, size: 110 KB).

TECHNICAL FIELD

This invention is in the field of in vitro assays for assessing the potency of protein-containing vaccines for protecting against *Neisseria meningitidis* (meningococcus).

BACKGROUND ART

Unlike live vaccines that are quantified by in vitro titration, the potency of inactivated or subunit vaccines normally requires an in vivo test for each batch prior to its release for public use [1], although a number of exceptions exist e.g. the SRID (single radial immunodiffusion) potency test for the influenza vaccine and the use of ELISA for hepatitis B vaccines.

Typical in vivo tests involve an immunisation-challenge test using small rodents (mice or rats) as the experimental model. Depending on the type of vaccine, different endpoints are used, such as death/survival ratios (whole cell pertussis, diphtheria toxoid and tetanus toxoid, rabies vaccine), clinical signs (diphtheria, tetanus) or colonisation (whole cell and acellular pertussis). By establishing a dose-response curve in parallel to a standard preparation with known potency, the potency of the vaccine can be expressed relative to that preparation e.g. in standard units.

A challenge model is not always available. In those cases potency testing is usually limited to serological responses, with antibody responses being measured after immunisation of test animals. At least part of the functionality of these antibodies can be determined by their ability to neutralise the pathogen in vitro or to their ability to kill bacteria in the presence of complement (such as the serum bactericidal antibody assay, or SBA, for meningococcus).

The SBA assay is useful but cumbersome, and involves the sacrifice of many mice. As explained in reference 1 it is thus desirable to provide in vitro alternatives for assessing vaccine potency.

One in vitro assay for analysing MenB vaccines is the "MATS" ELISA test disclosed in references 2 and 3. The relative potency measured by MATS was shown to correlate with the ability of MenB strains to be killed in SBA.

The MATS test is used to evaluate the strain coverage of a MenB vaccine, rather than to analyse the vaccine's immunogenicity. There remains a need for further and improved in vitro assays for assessing the immunogenicity of meningococcal vaccines. Such in vitro assays could be used to confirm that a particular vaccine will have an expected in vivo activity in human recipients.

DISCLOSURE OF THE INVENTION

The invention uses binding assays, such as ELISA, for analysing a meningococcal vaccine. The assay uses antibodies which bind to meningococcal proteins within the vaccine, and in particular monoclonal antibodies which are bactericidal for meningococcus and/or which recognise conformational epitopes within the meningococcal proteins. By performing the assay on a series of dilutions of a test vaccine, and by comparing the results with those obtained using a standard or reference vaccine of known potency, it is possible to determine the relative potency of the test vaccine. This value can be used as a parameter for determining whether a manufactured batch of a vaccine is suitable for release to the public, or whether it has experienced a production failure and so should not be used. Assays of the invention are particularly useful for analysing vaccines which contain multiple different antigens and/or which contain adsorbed antigen(s).

Thus the invention provides a binding assay for in vitro analysis of a meningococcal vaccine sample, comprising steps of: (i) permitting a meningococcal protein immunogen within the sample to interact with a monoclonal antibody which either (a) is bactericidal for meningococcus or (b) recognises a conformational epitope in the meningococcal antigen; then (ii) measuring the interaction between the immunogen and antibody from step (i).

The invention also provides an assay for in vitro analysis of a meningococcal test vaccine sample, comprising steps of: (i) performing the above binding assay on the test sample and, optionally, on at least one dilution of the test sample; (ii) performing the above binding assay on a standard vaccine sample and, optionally, on at least one dilution of the standard vaccine sample; and (iii) comparing the results from steps (i) and (ii) to determine the potency of immunogen(s) in the test vaccine relative to the potency of immunogen(s) in the standard vaccine.

The invention also provides a process for analysing a bulk vaccine, comprising steps of: (i) assaying the relative potency of immunogen(s) in the bulk as described above; and, if the results of step (i) indicate an acceptable relative potency, (ii) preparing unit doses of vaccine from the bulk.

The invention also provides a process for analysing a batch of vaccine, comprising steps of: (i) assaying the relative potency of immunogen(s) in at least one vaccine from the batch as described above; and, if the results of step (i) indicate an acceptable relative potency, (ii) releasing further vaccines from the batch for in vivo use.

The invention also provides a competitive ELISA assay for in vitro analysis of a meningococcal vaccine sample, wherein the assay uses (i) a solution-phase anti-vaccine monoclonal antibody (ii) an immobilised antigen which is recognised by the anti-vaccine antibody, and (iii) a labelled antibody which binds to the anti-vaccine antibody, wherein the antibody either (a) is bactericidal for meningococcus or (b) recognises a conformational epitope in the meningococcal antigen.

The invention also provides a binding assay for in vitro analysis of a meningococcal vaccine sample, wherein the assay uses immunogens in a vaccine to inhibit the binding of a monoclonal antibody to a control antigen, wherein the monoclonal antibody binds to both an immunogen in the vaccine and the control antigen.

The invention also provides a vaccine which has been released following use of an assay as described herein.

The invention also provides a kit for performing the assay of the invention. This kit may include e.g. a microwell plate, a microwell plate including well-immobilised immunogens, a dilution buffer, and/or an anti-immunogen antibody.

Binding Assays and ELISA Formats

The invention uses a binding immunoassay. Typically this will be an enzyme-linked immunosorbent assay (ELISA) as is well known in the art. The invention can use any ELISA format, including those conventionally known as direct ELISA, indirect ELISA, sandwich ELISA, and competitive ELISA.

Step (i) of the ELISA assay of the invention involves permitting a meningococcal protein immunogen within the sample to interact with a monoclonal antibody. The characteristics of this interaction (e.g. homogeneous or heterogeneous) will vary according to the chosen ELISA format. The interaction between the monoclonal antibody and the immunogen is then detected in step (ii). As typical for ELISA, the interaction can be measured quantitatively, such that step (ii) provides a result which indicates the concentration of the monoclonal antibody's target epitope within the vaccine sample. By using a monoclonal antibody which binds to a bactericidal or conformational epitope, the result in step (ii) indicates the concentration of the corresponding functional epitope in the vaccine sample, and can distinguish between immunogens which retain the relevant epitope (and function) and those which have lost the epitope (e.g. due to denaturation, aggregation or breakdown during storage or by mishandling). By comparison with values obtained with a standard vaccine of known potency, results from step (ii) can be used to calculate relative potency of a test vaccine.

The preferred ELISA format for use with the invention is the competitive ELISA (FIG. 5). In this format the vaccine sample is incubated with the monoclonal antibody (primary antibody) so that complexes can form between the antibody and immunogens in the sample. These complexes are then added to a container in which competitor antigens are immobilised. Antibody which is not complexed with immunogens from the vaccine sample is able to bind to these immobilised competitor antigens; if the sample contains a lot of target for the antibody then there will be less uncomplexed antibody to bind to the immobilised competitor antigens, whereas less target in the sample (whether due to lower amounts of immunogen, for example after dilution, or to loss of the antibody's epitope, for example after denaturation of immunogens) leads to more uncomplexed antibody. The antibody which is bound to the immobilised competitor antigens (after usual washing steps, etc.) can then be detected by adding a labelled secondary antibody which binds to the monoclonal anti-vaccine (i.e. primary) antibody. The label is used to quantify the amount of immobilised primary antibody in the normal ways. The use of competitive ELISA avoids the need to have two different anti-immunogen antibodies which recognise different epitopes on the same immunogen, and also can give better results in vaccines which include multiple different immunogen components. It also permits the test vaccine to be analysed directly, without requiring any manipulation prior to testing (although such manipulations can be performed if desired).

Suitable competitor antigens for immobilisation include the meningococcal proteins which are present in the vaccine, or proteins comprising these vaccine proteins (e.g. fusion proteins), or proteins comprising fragments of the vaccine proteins (e.g. truncated forms). The immobilised competitor antigen must retain the epitope recognised by the relevant monoclonal antibody, so that it can compete with the vaccine's immunogens for binding to the antibody. Typically this can be achieved by immobilising antigen from fresh batches of bulk vaccine or, preferably, from fresh batches of bulk purified immunogen prior to preparation of bulk vaccine.

Labelling of antibodies in an ELISA can take various forms. In the preferred competitive format the secondary antibody is labelled. In an ELISA the antibody is labelled with an enzyme, which is then used to catalyse a reaction whose product is readily detectable. The linked enzyme can cause a detectable change in an enzyme substrate which is added to the labelled antibody after it becomes immobilised e.g. to modify a substrate in a manner which causes a colour change. For example the enzyme may be a peroxidase (e.g. horseradish peroxidase, HRP), or a phosphatase (e.g. alkaline phosphatase, AP). Other enzymes can also be used e.g. laccase, β-galactosidase, etc.

The choice of substrate will depend on the choice of linked enzyme. Moreover, substrates differ in terms of cost, ease-of-use, sensitivity (i.e. lower limit of detection) and compatibility with available imaging equipment. These parameters are familiar to those skilled in ELISA. Preferred substrates undergo a colorimetric change, a chemiluminescent change, or a chemifluorescent change when contacted with the linked enzyme. Colorimetric substrates (and their enzymatic partners) include, but are not limited to: PNPP or p-Nitrophenyl Phosphate (AP); ABTS or 2,2'-Azinobis[3-ethylbenzothiazoline-6-sulfonic acid] (HRP); OPD or o-phenylenediamine dihydrochloride (HRP); and TMB or 3,3',5,5'-tetramethylbenzidine (HRP). Chemiluminescent substrates include luminol or 5-amino-2,3-dihydro-1,4-phthalazinedione (HRP), particularly in the presence of modified phenols such as p-iodophenol. Chemifluorescent substrates include p-hydroxyhydrocinnamic acid. Various proprietary substrates are also available and these can be used with the invention if desired e.g. QuantaBlu, QuantaRed, SuperSignal, Turbo TMB, etc.

Where an ELISA reagent is immobilised on a solid surface, this surface take various forms. Usually the reagent is immobilised on a plastic surface, such as a surface made from polystyrene, polypropylene, polycarbonate, or cyclo-olefin. The plastic will usually be transparent and colourless, particularly when using chromogenic enzyme substrates. White or black plastics may be preferred used when using luminescent or fluorescent substrates, as known in the art. The plastic will generally be used in the form of a microwell plate (microtitre plate) as known in the art for ELISA (a flat plate having multiple individual and reaction wells). Such plates include those with 6, 24, 96, or 384 sample wells, usually arranged in a 2:3 rectangular matrix. Microwell plates facilitate the preparation of dilution series and also the transfer of materials from one plate to another while maintaining spatial relationships e.g. in the step of transferring a mixture of antibody and vaccine into a different microwell plate for measuring the interaction between the antibody and vaccine.

During an ELISA it may be desirable to add a blocking reagent and/or detergent e.g. to reduce non-specific binding interactions which might distort the assay's results. Blocking procedures are familiar to people working in the ELISA field.

In addition to the ELISA formats discussed above, the invention can use any suitable variants of ELISA, such as M&P ELISA or ELISA Reverse [4], the rapid ELISA of reference 5, etc., and can also be extended to use alternatives to ELISA, such as flow injection immunoaffinity analysis (FIIAA), AlphaLISA or AlphaScreen[6], dissociation-enhanced lanthanide fluorescent immunoassay (DELFIA), ELAST, the BIO-PLEX Suspension Array System, MSD, etc. Any of these binding assays can be used.

As an alternative to using a conjugated enzyme as the label, other labelling is possible. For instance, other indirect labels (i.e. alternative to enzymes) can be used, but it is also possible to label the antibody by conjugation to a direct label such as a coloured particle, an electrochemically active reagent, a redox reagent, a radioactive isotope, a fluorescent label or a luminescent label.

As a further alternative, the primary antibody can be conjugated to a high affinity tag such as biotin, avidin or streptavidin. An enzyme conjugated to a ligand for the tag, such as avidin, streptavidin or biotin can then be used to detect immobilised primary antibody.

Any of these variations can be used within the scope and spirit of the overall invention.

In some ELISA formats, rather than labelling a secondary antibody, the anti-vaccine monoclonal antibody (whether a bactericidal antibody or one which recognises a conformational epitope) will be labelled. Thus the invention provides a monoclonal antibody which immunospecifically binds to a meningococcal protein (such as NHBA, etc., as disclosed herein) and which is conjugated to an enzyme (such as AP or HRP). Immunospecific binding can be contrasted with non-specific binding, and antibodies of the invention will thus have a higher affinity (e.g. at least 100-fold higher affinity) for the meningococcal target protein than for an irrelevant control protein, such as bovine serum albumin.

The Vaccine Sample

Assays of the invention are used to analyse vaccines. The assay is performed on at least one sample of the vaccine, and this analysis reveals information about the sampled vaccine. The assay can be performed on a sample(s) taken from a bulk vaccine, in which case the assay's results can be used to determine the fate of that bulk e.g. whether it is suitable for further manufacturing use (e.g. for preparing packaged doses of the vaccine), or whether it should instead be modified or discarded. The assay can also be performed on a sample(s) taken from a batch of vaccines, in which case the assay's results can be used to determine the fate of that batch e.g. whether the batch is suitable for release for use by healthcare professionals. Usually, enough samples will be taken from bulks/batches to ensure compliance with statistical practices which are normal for vaccine release assays. Testing of batches of final vaccine (formulated and packaged) in the form in which they would be released to the public is most useful.

The vaccine sample can be analysed at full strength i.e. in the form in which it is taken from the bulk or batch. In some cases, however, it is useful to analyse the vaccine at a fraction of full strength e.g. after dilution. The most useful assays analyse a series of strengths, the strongest of which may be a full strength sample or may be at fractional strength. Dilutions will typically be achieved using buffer rather than with plain water. Such buffers can sometimes include surfactants such as polysorbate 20 or polysorbate 80.

It is useful to analyse a series of dilutions of the vaccine. For instance, serial 1:2, 1:5 or 1:10 (by volume) dilutions can be used. The dilution series will include at least 2 members, but usually will include more e.g. 5, 10, or more members. For instance, 9 serial dilutions at 1:2 gives 10 samples at $1:2^0$, $1:2^1$, $1:2^2$, . . . , $1:2^9$, and $1:2^{10}$-fold strengths relative to the strongest sample. The dilution series can be tested using the assays of the invention to provide a series of measurements which can be plotted (literally or notionally) against dilution. This series of measurements can be used to assess the vaccine's relative potency, as described below. The vaccine includes at least one meningococcal protein immunogen i.e. a protein which, when administered to human beings, elicits a bactericidal immune response. Various such proteins are known in the art, including but not limited to NHBA, fHbp and NadA as found in the BEXSERO™ product [7,8]. Further protein immunogens which can be analysed are HmbR, NspA, NhhA, App, Omp85, TbpA, TbpB, and Cu,Zn-superoxide dismutase. A vaccine may include one or more of these various antigens e.g. it can include each of NHBA, fHbp and NadA. It can also include variant forms of a single antigen e.g. it can include more than one variant of meningococcal fHbp (i.e. two fHbp proteins with different sequences [9]), using different monoclonal anti-fHbp antibodies to recognise each different variant separately.

The vaccine can include meningococcal vesicles i.e. any proteoliposomic vesicle obtained by disruption of or blebbing from a meningococcal outer membrane to form vesicles therefrom that retain antigens from the outer membrane. Thus this term includes, for instance, OMVs (sometimes referred to as 'blebs'), microvesicles (MVs) and 'native OMVs' ('NOMVs'). Various such vesicles are known in the art (e.g. see references 10 to 24) and any of these can be included within a vaccine to be analysed by the invention. In some embodiments, however, the vaccine is vesicle-free. Where a vaccine does include vesicles it is preferred to use a competitive ELISA format as this tends to give better results in samples which contain multiple components.

An analysed vaccine can preferably elicit an immune response in human beings which is protective against serogroup B meningococcus. For instance, the vaccine may elicit an immune response which is protective at least against a prototype serogroup B strain such as MC58, which is widely available (e.g. ATCC BAA-335) and was the strain sequenced in reference 25. Other strains can also be tested for vaccine efficacy [2] but a response against MC58 is easily tested.

A preferred vaccine which can be analysed according to the invention is BEXSERO™ [7]. This vaccine includes three different recombinant proteins, consisting of amino acid sequences SEQ ID NO: 4, SEQ ID NO: 5, and SEQ ID NO: 6. It also contains NZ98/254 outer membrane vesicles.

In addition to meningococcal protein immunogens, a vaccine can include other immunogens. These can be non-protein immunogens from meningococcus and/or immunogens from other bacteria and/or immunogens from non-bacterial pathogens, such as viruses. Thus, for instance, an analysed vaccine might include: (a) one or more capsular saccharides from meningococci e.g. from serogroups A, C, W135 and/or Y, as in the MENVEO, MENACTRA, and NIMENRIX products which all include conjugated capsular saccharides; (b) an antigen from *Streptococcus pneumoniae*, such as a saccharide (typically conjugated), as in the PREVNAR and SYNFLORIX products; (c) an antigen from hepatitis B virus, such as the surface antigen HBsAg; (d) an antigen from *Bordetella pertussis*, such as pertussis holotoxin (PT) and filamentous haemagglutinin (FHA) from *B. pertussis*, optionally also in combination with pertactin and/or agglutinogens 2 and 3; (e) a diphtheria antigen, such as a diphtheria toxoid; (f) a tetanus antigen, such as a tetanus toxoid; (g) a saccharide antigen from *Haemophilus influenzae* B (Hib), typically conjugated; and/or (h) inactivated poliovirus antigens.

The vaccine is a pharmaceutical composition and so, in addition to its immunogens, typically includes a pharmaceutically acceptable carrier, and a thorough discussion of such carriers is available in reference 26.

The pH of an analysed vaccine is usually between 6 and 8, and more preferably between 6.5 and 7.5 (e.g. about 7). Stable pH in an analysed vaccine may be maintained by the use of a buffer e.g. a Tris buffer, a citrate buffer, phosphate buffer, or a histidine buffer. Thus an analysed vaccine will generally include a buffer.

An analysed vaccine may be sterile and/or pyrogen-free. Compositions of the invention may be isotonic with respect to humans.

An analysed vaccine comprises an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 μg (e.g. 50 μg) per immunogen can be useful.

Analysed vaccines may include an immunological adjuvant. Thus, for example, they may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref. 27), or mixtures thereof. The salts can take any suitable form (e.g. gel, crystalline, amorphous, etc.), with adsorption of antigen to the salt being preferred. The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred. Aluminium hydroxide adjuvants are particularly suitable for use with meningococcal vaccines. The invention has been shown to give useful results despite the adsorption of protein immunogens within the vaccine, and analysis is possible without requiring a desorption step (i.e. analysis can be performed without a desorption pre-treatment of the vaccine). Where a vaccine includes adsorbed immunogen it is preferred to use a competitive ELISA format as this tends to give better results.

Analysed vaccines may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Analysed vaccines may comprise detergent e.g. a TWEEN™ (polysorbate), such as TWEEN™ 80. Detergents are generally present at low levels e.g. <0.01%. Analysed vaccines may include residual detergent (e.g. deoxycholate) from OMV preparation. The amount of residual detergent is preferably less than 0.4 μg (more preferably less than 0.2 μg) for every μg of MenB protein.

If an analysed vaccine includes LOS, the amount of LOS is preferably less than 0.12 μg (more preferably less than 0.05 μg) for every μg of protein.

Analysed vaccines may include sodium salts (e.g. sodium chloride) to give tonicity. A concentration of 10±2 mg/ml NaCl is typical e.g. about 9 mg/ml.

The Standard Vaccine

The assay of the invention can provide quantitative information about the amount of functional epitopes in a vaccine. If this amount is compared to the amount in a vaccine of known potency then it is possible to calculate the relative potency of a test vaccine. Thus in some embodiments the analysed vaccine is a standard vaccine which has known potency in an in vivo assay e.g. it has a known SBA titre. In other embodiments the analysed vaccine is a test vaccine which does not have a known potency in an in vivo assay. In further embodiments the assay is used to analyse both a standard vaccine and a test vaccine, and the results of the analysis of the test vaccine are compared to the analysis of the standard vaccine, and this comparison is used to express the test vaccine's potency relative to the known potency of the standard vaccine.

For instance, after manufacture of a new bulk preparation of BEXSERO™, or after storage of a batch or bulk of manufactured vaccine, a test sample from the batch/bulk can be tested using the assay of the invention, and the results can be compared to those obtained with BEXSERO™ having known in vivo potency. This comparison will reveal whether the new/stored batch/bulk (the test sample) is as potent as it should be. If so, the batch/bulk can be released for further use; if not, it can be investigated and/or discarded. For instance, unit doses can be prepared from the bulk, or the batch can be released for public distribution and use.

For assessing relative potency it is useful to analyse the test vaccine and the standard vaccine at a variety of strengths. As discussed above, a series of dilutions of the vaccines can be analysed. The dilution series can be tested using the assays of the invention to provide a curve (literally or notionally) of binding assay results against dilution. This curve can be compared to a standard curve (i.e. the same curve, but obtained with the standard vaccine) to determine relative potency. For instance, by plotting the logarithm of the binding titer against the logarithm of dilution for the test and reference vaccines, the horizontal distance between the two parallel regression lines indicates relative potency (no horizontal separation indicating a relative potency of 100% or 1.0).

To simplify comparisons, the dilutions used for the test vaccine should be the same as those used for the reference vaccine (e.g. a series of 1:2, 1:5, or 1:10 dilutions for both vaccines).

A test for relative potency can be carried out multiple times in order to determine variance of the assay e.g. multiple times (duplicate, triplicate, etc.) on a single sample, and/or performed on multiple samples from the same bulk/batch. The invention can involve determining the variation in such multiple assays (e.g. the coefficient of variation) as a useful parameter, and in some embodiments the results of the assay are considered as useful only where variation falls within acceptable limits e.g. <15%. Sometimes a wider variation is permitted e.g. <20%, depending whether tests are performed within (intra-assay) or in different (inter-assay) experimental sessions.

Where a vaccine includes multiple different immunogen, the potency of each of these is ideally tested separately. These results can then be combined for an analysis of the vaccine sample as a whole, but it is useful to identify the specific cause of any loss of overall potency.

The Antibody

Assays of the invention use monoclonal antibodies which recognise protein immunogens which are present within the analysed vaccines. The invention can use antibodies which are bactericidal for meningococcus and/or which recognise conformational epitopes in the protein immunogens. In both cases the antibodies can thus distinguish between functional immunogen and denatured or non-functional immunogen. The use of bactericidal antibodies is preferred.

Determining whether an antibody is bactericidal against meningococcus is routine in the art, and can be assessed by SBA [28-31]. Reference 32 reports good inter-laboratory reproducibility of this assay when using harmonised procedures. SBA can be run against strain H44/76 (reference strain 237 from the PubMLST database; strain designation B: P1.7,16: F3-3: ST-32 (cc32); also known as 44/76-3 or Z3842). For present purposes, however, an antibody can be regarded as bactericidal if it kills strain MC58 using human complement.

Determining whether an antibody recognises a conformational epitope is also straightforward. For instance, the antibody can be tested against a panel of linear peptide fragments from the target antigen (e.g. using the Pepscan technique) and the binding can be compared to the antibody's binding against the complete antigen. As an alternative, binding can be compared before and after denaturation of the target antigen.

Assays of the invention can use a single monoclonal antibody or a mixture of monoclonal antibodies. Typically a vaccine will include multiple different immunogens and each of these will require a different monoclonal antibody for its analysis. Thus an assay can use: a single monoclonal antibody which recognises a single immunogen; a plurality of different monoclonal antibodies which recognise a single immunogen (typically different epitopes on the immunogen); a plurality of different monoclonal antibodies which recognise a plurality of different immunogens, in which there is one or more antibody/s per immunogen (typically recognising different epitopes if they target the same immunogen). Rather than perform a single assay to recognise multiple immunogens simultaneously, it is preferred to perform multiple assays with a single monoclonal antibody per assay. These results can then be combined for an overall analysis of the vaccine sample. By using multiple assays, each immunogen within a multi-immunogen vaccine can be assessed separately e.g. to isolate the cause of any loss of potency relative to a standard vaccine.

An antibody can be tested to ensure that it does not cross-react with other antigens which might be present in a vaccine. This test is straightforward, and such cross-reacting antibodies can either be used with caution and proper controls, or can be rejected in favour of antibodies which do not have the cross-reacting activity.

To facilitate determination of relative potency, the monoclonal antibody should show a linear binding response when a target antigen diluted i.e. dilution of the target antigen should bring about a corresponding reduction in binding by the antibody. Linearity can be assessed by linear regression e.g. to have $R^2 \geq 0.95$.

The monoclonal antibodies can be obtained from any suitable species e.g. murine, rabbit, sheep, goat, or human monoclonal antibodies. Advantageously, the chosen species can be selected such that secondary antibodies are readily available e.g. labelled goat anti-mouse secondary antibodies are easy to obtain, so mouse monoclonal antibodies are easily usable in ELISA.

The monoclonal antibodies can have any heavy chain type e.g. it can have $\alpha$, $\delta$, $\varepsilon$, $\gamma$ or $\mu$ heavy chain, giving rise respectively to antibodies of IgA, IgD, IgE, IgG, or IgM class. Classes may be further divided into subclasses or isotypes e.g. IgG1, IgG2, IgG3, IgG4, IgA, IgA2, etc. Antibodies may also be classified by allotype e.g. a $\gamma$ heavy chain may have G1m allotype a, f, x or z, G2m allotype n, or G3m allotype b0, b1, b3, b4, b5, c3, c5, g1, g5, s, t, u, or v; a $\kappa$ light chain may have a Km(1), Km(2) or Km(3) allotype. IgG monoclonal antibodies are preferred. A native IgG antibody has two identical light chains (one constant domain $C_L$ and one variable domain $V_L$) and two identical heavy chains (three constant domains $C_H1$ $C_H2$ & $C_H3$ and one variable domain $V_H$), held together by disulfide bridges.

The monoclonal antibodies can have any light chain type e.g. it can have either a kappa ($\kappa$) or a lambda ($\lambda$) light chain.

The term "antibody" is not limited to native antibodies, as naturally found in mammals. The term encompasses any similar molecule which can perform the same role in an immunoassay such as ELISA. Thus the antibody may be, for example, a fragment of a native antibody which retains antigen binding activity (e.g. a Fab fragment, a Fab' fragment, a F(ab')2 fragment, a Fv fragment), a "single-chain Fv" comprising a VH and VL domain as a single polypeptide chain, a "diabody", a "triabody", a single variable domain or VHH antibody, a "domain antibody" (dAb), a chimeric antibody having constant domains from one organism but variable domains from a different organism, a CDR-grafted antibody, etc. The antibody may include a single antigen binding site (e.g. as in a Fab fragment or a scFv) or multiple antigen binding sites (e.g. as in a F(ab')2 fragment or a diabody or a native antibody). Where an antibody has more than one antigen-binding site, however, it is preferably a mono-specific antibody i.e. all antigen-binding sites recognize the same antigen. The antibody may have a constant domain (e.g. including $C_H$ or $C_L$ domains), but this is not always required. Thus the term "antibody" as used herein encompasses a range of proteins having diverse structural features (usually including at least one immunoglobulin domain having an all-$\beta$ protein fold with a 2-layer sandwich of anti-parallel $\beta$-strands arranged in two $\beta$-sheets), but all of the proteins possess the ability to bind to the target protein immunogens.

The term "monoclonal" as originally used in relation to antibodies referred to antibodies produced by a single clonal line of immune cells, as opposed to "polyclonal" antibodies that, while all recognizing the same target protein, were produced by different B cells and would be directed to different epitopes on that protein. As used herein, the word "monoclonal" does not imply any particular cellular origin, but refers to any population of antibodies that all have the same amino acid sequence and recognize the same epitope(s) in the same target protein(s). Thus a monoclonal antibody may be produced using any suitable protein synthesis system, including immune cells, non-immune cells, acellular systems, etc. This usage is usual in the field e.g. the product datasheets for the CDR grafted humanised antibody Synagis™ expressed in a murine myeloma NS0 cell line, the humanised antibody Herceptin™ expressed in a CHO cell line, and the phage-displayed antibody Humira™ expressed in a CHO cell line all refer the products as monoclonal antibodies. The term "monoclonal antibody" thus is not limited regarding the species or source of the antibody, nor by the manner in which it is made.

Known monoclonal antibodies can be used with the invention, or new monoclonal antibodies can be generated using known techniques (e.g. injection of a reference vaccine's immunogen into mice with Freund's complete adjuvant), followed by screening for those with suitable properties e.g. for bactericidal activity, etc. The invention does not require the use of particular known antibodies, but a number of antibodies useful for analysis of the immunogens in BEXSERO™ are described below:

- A suitable monoclonal antibody for assaying NHBA as found in the BEXSERO™ product is the 42A4A2 antibody (murine IgG1) which likely recognises a conformational epitope.
- Suitable monoclonal antibodies for assaying fHbp as found in the BEXSERO™ product include, but are not limited to, the MAb502 antibody [33,34], the 12C1/D7 antibody (see below) and the 11F10/G6 antibody (see below). These three antibodies are all bactericidal. MAb502 (murine IgG2a) does not give good linearity when diluted and so the other two antibodies (both murine IgG2b) are preferable. Two other useful anti-fHbp monoclonal antibodies are 30G11/H3 and 14B3/D4 (see below) The JAR3 and JARS antibodies (ref. 35; GenBank VL and VH genes are JF715927, F715926, JF715929 and JF715928) can also be used, as can other prior art JAR antibodies e.g. up to JAR35 [36]. The anti-fHbp monoclonal antibody can bind to a single variant of fHbp, or can bind to more than one variant (such as the JAR3 and JARS antibodies, as reported in reference 37).
- A suitable monoclonal antibody for assaying NadA as found in the BEXSERO™ product is the bactericidal 9F11/19 antibody (murine IgG2b).

Assaying a vesicle component in a vaccine can use any antigen in the vesicle, but it is convenient to use anti-PorA antibodies as these are readily available for serosubtype analysis (e.g. from NIBSC). Thus for assaying the OMV component as found in the BEXSERO™ product a suitable monoclonal antibody recognises serosubtype P1.4.

A secondary antibody used with the invention (e.g. in the assay's competitive format) can recognise the primary antibody when the primary antibody has become immobilised. The secondary antibody is typically polyclonal. For instance, if the primary antibody is murine then the secondary antibody can be an anti-murine antibody e.g. goat anti-mouse IgG. Suitable criteria for choosing secondary antibodies are well known in the ELISA field.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 38-44, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%. Where the invention concerns an "epitope", this epitope may be a B-cell epitope and/or a T-cell epitope, but will usually be a B-cell epitope. Such epitopes can be identified empirically (e.g. using PEPSCAN [45,46] or similar methods), or they can be predicted (e.g. using the Jameson-Wolf antigenic index [47], matrix-based approaches [48], MAPITOPE [49], TEPITOPE [50,51], neural networks [52], OptiMer & EpiMer [53, 54], ADEPT [55], Tsites [56], hydrophilicity [57], antigenic index [58] or the methods disclosed in references 59-63, etc.). Epitopes are the parts of an antigen that are recognised by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and % homology or sequence identity can be determined using software programs known in the art, for example those described in section 7.7.18 of ref. 64. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 65.

The word "substantially" does not exclude "completely" e.g. a composition which is "substantially free" from Y may be completely free from Y. Where necessary, the word "substantially" may be omitted from the definition of the invention.

Meningococcal Protein Immunogens

NHBA (Neisserial Heparin Binding Antigen)

NHBA [68] was included in the published genome sequence for meningococcal serogroup B strain MC58 [25] as gene NMB2132 (GenBank accession number GI:7227388; SEQ ID NO: 9 herein). Sequences of NHBA from many strains have been published since then. For example, allelic forms of NHBA (referred to as protein '287') can be seen in FIGS. 5 and 15 of reference 66, and in example 13 and FIG. 21 of reference 67 (SEQ IDs 3179 to 3184 therein). Various immunogenic fragments of NHBA have also been reported.

Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 9.

The most useful NHBA antigens can elicit antibodies which, after administration to a subject, can bind to a meningococcal polypeptide consisting of amino acid sequence SEQ ID NO: 9. Advantageous NHBA antigens for use with the invention can elicit bactericidal anti-meningococcal antibodies after administration to a subject.

Over-expression of NHBA has previously been achieved in various ways e.g. introduction of a NHBA gene under the control of an IPTG-inducible promoter [68].

NadA (Neisserial Adhesin A)

The NadA antigen was included in the published genome sequence for meningococcal serogroup B strain MC58 [25] as gene NMB1994 (GenBank accession number GI:7227256; SEQ ID NO: 10 herein). The sequences of NadA antigen from many strains have been published since then, and the protein's activity as a Neisserial adhesin has been well documented. Various immunogenic fragments of NadA have also been reported.

Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10.

The most useful NadA antigens can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. SEQ ID NO: 6 is one such fragment.

HmbR

The full-length HmbR sequence was included in the published genome sequence for meningococcal serogroup B strain MC58 [25] as gene NMB1668 (SEQ ID NO: 7 herein). Reference 69 reports a HmbR sequence from a different strain (SEQ ID NO: 8 herein), and reference 70 reports a further sequence (SEQ ID NO: 19 herein). SEQ ID NOs: 7 and 8 differ in length by 1 amino acid and have 94.2% identity. SEQ ID NO: 19 is one amino acid shorter than SEQ ID NO: 7 and they have 99% identity (one insertion, seven differences) by CLUSTALW. The invention can use any such HmbR polypeptide.

The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7.

Preferred fragments of j amino acids comprise an epitope from SEQ ID NO: 7. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 71. Fragments that retain a transmembrane sequence are useful, because they can be displayed on the bacterial surface e.g. in vesicles. Examples of long fragments of HmbR correspond to SEQ ID NOs: 15 and 16. If soluble HmbR is used, however, sequences omitting the transmembrane sequence, but typically retaining epitope(s) from the extracellular portion, can be used.

The most useful HmbR antigens can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

fHbp (Factor H Binding Protein)

The fHbp antigen has been characterised in detail. It has also been known as protein '741' [SEQ IDs 2535 & 2536 in ref. 67], 'NMB1870', 'GNA1870' [72-74], 'P2086', 'LP2086' or 'ORF2086' [75-77]. It is naturally a lipoprotein and is expressed across all meningococcal serogroups. The structure of fHbp's C-terminal immunodominant domain ('fHbpC') has been determined by NMR [78]. This part of the protein forms an eight-stranded β-barrel, whose strands are connected by loops of variable lengths. The barrel is preceded by a short α-helix and by a flexible N-terminal tail.

The fHbp antigen falls into three distinct variants [79] and it has been found that serum raised against a given family is bactericidal within the same family, but is not active against strains which express one of the other two families i.e. there is intra-family cross-protection, but not inter-family cross-protection. The invention can use a single fHbp variant, but a vaccine will usefully include a fHbp from two or three of the variants. Thus it may use a combination of two or three different fHbps, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3.

The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92, 93, 94, 95, 96, 97, 98, 99, 99.5, or more. The value of c is at least 85 e.g. 86, 87, 88, 89, 90, 91, 92, 93, 94, 95, 96, 97, 98, 99, 99.5, or more. The values of a, b and c are not intrinsically related to each other.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

Where the invention uses a single fHbp variant, a composition may include a polypeptide comprising (a) an amino acid sequence having at least a %, sequence identity to SEQ ID NO: 1 and/or comprising an amino acid sequence consisting of a fragment of at least x contiguous amino acids from SEQ ID NO: 1; or (b) an amino acid sequence having at least b %, sequence identity to SEQ ID NO: 2 and/or comprising an amino acid sequence consisting of a fragment of at least y contiguous amino acids from SEQ ID NO: 2; or (c) an amino acid sequence having at least c %, sequence identity to SEQ ID NO: 3 and/or comprising an amino acid sequence consisting of a fragment of at least z contiguous amino acids from SEQ ID NO: 3.

Where the invention uses a fHbp from two or three of the variants, a composition may include a combination of two or three different fHbps selected from: (a) a first polypeptide, comprising an amino acid sequence having at least a %, sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least b %, sequence identity to SEQ ID NO: 2 and/or comprising an amino acid sequence consisting of a fragment of at least y contiguous amino acids from SEQ ID NO: 2; and/or (c) a third polypeptide, comprising an amino acid sequence having at least c %, sequence identity to SEQ ID NO: 3 and/or comprising an amino acid sequence consisting of a fragment of at least z contiguous amino acids from SEQ ID NO: 3. The first, second and third polypeptides have different amino acid sequences.

Where the invention uses a fHbp from two of the variants, a composition can include both: (a) a first polypeptide, comprising an amino acid sequence having at least a %, sequence identity to SEQ ID NO: 1 and/or comprising an amino acid sequence consisting of a fragment of at least x contiguous amino acids from SEQ ID NO: 1; and (b) a second polypeptide, comprising an amino acid sequence having at least b %, sequence identity to SEQ ID NO: 2 and/or comprising an amino acid sequence consisting of a fragment of at least y contiguous amino acids from SEQ ID NO: 2. The first and second polypeptides have different amino acid sequences.

Where the invention uses a fHbp from two of the variants, a composition can include both: (a) a first polypeptide, comprising an amino acid sequence having at least a %, sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least c % sequence identity to SEQ ID NO: 3 and/or comprising an amino acid sequence consisting of a fragment of at least z contiguous amino acids from SEQ ID NO: 3. The first and second polypeptides have different amino acid sequences.

Another useful fHbp which can be used according to the invention is one of the modified forms disclosed, for example, in reference 80 e.g. comprising SEQ ID NO: 20 or 23 therefrom. These modified forms can elicit antibody responses which are broadly bactericidal against meningococci. SEQ ID NO: 77 in reference 80 is another useful fHbp sequence which can be used.

fHbp protein(s) in a OMV will usually be lipidated e.g. at a N-terminus cysteine. In other embodiments they will not be lipidated.

One vaccine which can be analysed by the methods of the invention includes two different variants of fHbp. The first variant can have amino acid sequence SEQ ID NO: 29, and the second can have amino acid sequence SEQ ID NO: 30. These are preferably lipidated at their N-terminus cysteines. This vaccine can include an aluminium phosphate adjuvant, and can also include a histidine buffer and polysorbate 80. Ideally it includes equal masses of the two different fHbp polypeptides.

NspA (Neisserial Surface Protein A)

The NspA antigen was included in the published genome sequence for meningococcal serogroup B strain MC58 [25] as gene NMB0663 (GenBank accession number GI:7225888; SEQ ID NO: 11 herein). The antigen was previously known from references 81 & 82. The sequences of NspA antigen from many strains have been published since then. Various immunogenic fragments of NspA have also been reported.

Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11.

The most useful NspA antigens can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

NhhA (Neisseria Hia Homologue)

The NhhA antigen was included in the published genome sequence for meningococcal serogroup B strain MC58 [25] as gene NMB0992 (GenBank accession number GI:7226232; SEQ ID NO: 12 herein). The sequences of NhhA antigen from many strains have been published since e.g. refs 66 & 83, and various immunogenic fragments of NhhA have been reported. It is also known as Hsf.

Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12.

The most useful NhhA antigens can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

App (Adhesion and Penetration Protein)

The App antigen was included in the published genome sequence for meningococcal serogroup B strain MC58 [25] as gene NMB1985 (GenBank accession number GI:7227246; SEQ ID NO: 13 herein). The sequences of App antigen from many strains have been published since then. It has also been known as 'ORF1' and 'Hap'. Various immunogenic fragments of App have also been reported.

Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13.

The most useful App antigens can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

Omp85 (85 kDa Outer Membrane Protein)

The Omp85 antigen was included in the published genome sequence for meningococcal serogroup B strain MC58 [25] as gene NMB0182 (GenBank accession number GI:7225401; SEQ ID NO: 14 herein). The sequences of Omp85 antigen from many strains have been published since then. Further information on Omp85 can be found in references 84 and 85. Various immunogenic fragments of Omp85 have also been reported.

Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14.

The most useful Omp85 antigens can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

TbpA

The TbpA antigen was included in the published genome sequence for meningococcal serogroup B strain MC58 [25] as gene NMB0461 (GenBank accession number GI:7225687; SEQ ID NO: 17 herein). The sequences of TbpA from many strains have been published since then. Various immunogenic fragments of TbpA have also been reported.

Preferred TbpA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 17; and/or (b) comprising a fragment of at least 'n' consecutive amino acids of SEQ ID NO: 17, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 17.

The most useful TbpA antigens can elicit antibodies which, after administration to a subject, can bind to a meningococcal polypeptide consisting of amino acid sequence SEQ ID NO: 17. Advantageous TbpA antigens for use with the invention can elicit bactericidal anti-meningococcal antibodies after administration to a subject.

TbpB

The TbpB antigen was included in the published genome sequence for meningococcal serogroup B strain MC58 [25] as gene NMB1398 (GenBank accession number GI:7225686; SEQ ID NO: 18 herein). The sequences of TbpB from many strains have been published since then. Various immunogenic fragments of TbpB have also been reported.

Preferred TbpB antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 18; and/or (b) comprising a fragment of at least 'n' consecutive amino acids of SEQ ID NO: 18, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 18.

The most useful TbpB antigens can elicit antibodies which, after administration to a subject, can bind to a meningococcal polypeptide consisting of amino acid sequence SEQ ID NO: 18. Advantageous TbpB antigens for use with the invention can elicit bactericidal anti-meningococcal antibodies after administration to a subject.

Cu,Zn-Superoxide Dismutase

The Cu,Zn-superoxide dismutase antigen was included in the published genome sequence for meningococcal serogroup B strain MC58 [25] as gene NMB1398 (GenBank accession number GI:7226637; SEQ ID NO: 20 herein). The sequences of Cu,Zn-superoxide dismutase from many strains have been published since then. Various immunogenic fragments of Cu,Zn-superoxide dismutase have also been reported.

Preferred Cu,Zn-superoxide dismutase antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 20; and/or (b) comprising a fragment of at least 'n' consecutive amino acids of SEQ ID NO: 20, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 20.

The most useful Cu,Zn-superoxide dismutase antigens can elicit antibodies which, after administration to a subject, can bind to a meningococcal polypeptide consisting of amino acid sequence SEQ ID NO: 20. Advantageous Cu,Zn-superoxide dismutase antigens for use with the invention can elicit bactericidal anti-meningococcal antibodies after administration to a subject.

Monoclonal Antibodies

The invention also provides monoclonal antibodies which recognise meningococcal antigens. These can be used with the assays of the invention, or can be used more generally.

One antibody of the invention is "12C1/D7". Its $V_L$ region has amino acid sequence SEQ ID NO: 21 and its $V_H$ region has amino acid sequence SEQ ID NO: 22.

Another antibody of the invention is "11F10/G6". Its $V_L$ region has amino acid sequence SEQ ID NO: 23 and its $V_H$ region has amino acid sequence SEQ ID NO: 24.

Another antibody of the invention is "30G11/H3". Its $V_L$ region has amino acid sequence SEQ ID NO: 25 and its $V_H$ region has amino acid sequence SEQ ID NO: 26.

Another antibody of the invention is "14B3/D4". Its $V_L$ region has amino acid sequence SEQ ID NO: 27 and its $V_H$ region has amino acid sequence SEQ ID NO: 28.

The invention also provides monoclonal antibodies which bind to meningococcal antigens and which include the CDRs from the $V_L$ and $V_H$ regions of 12C1/D7, 11F10/G6, 30G11/H3, or 14B3/D4.

MODES FOR CARRYING OUT THE INVENTION

Figure 1A:
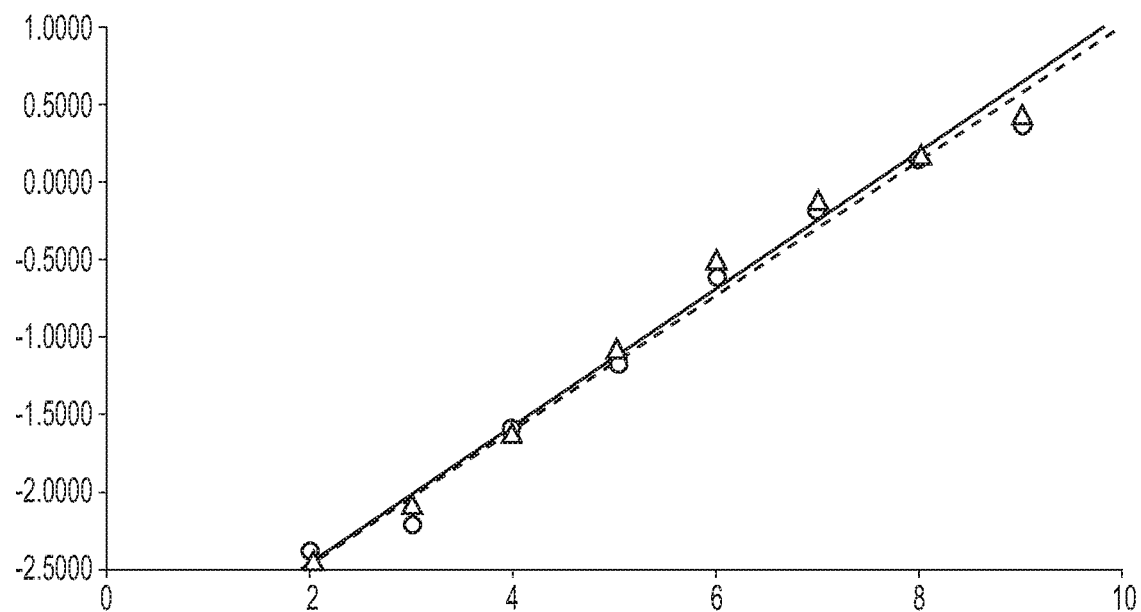
FIG. 1 shows relative potency plots for NHBA, fHbp, NadA and OMV immunogens in BEXSERO™ using monoclonal antibodies (A) 42A4A2 (B) MAb502 (C) 12C1/D7 (D) 11F10/G6 (E) 9F11/19 (F) Anti-PorA. Each plot shows $\log(OD_{405\text{-}620\ nm})$ against log(dilution). Circles show data for the standard vaccine; triangles for the test vaccine.

The BEXSERO™ product is described in reference 7, and it includes 50 µg of each of NadA (subvariant 3.1; SEQ ID NO: 6), fHbp subvariant 1.1 (as a GNA2091-fHbp fusion protein; SEQ ID NO: 5), and NHBA subvariant 1.2 (as a NHBA-GNA1030 fusion protein; SEQ ID NO: 4), adsorbed onto 1.5 mg aluminium hydroxide, and with 25 µg OMVs from *N. meningitidis* strain NZ98/254.

The following monoclonal antibodies are available:
(A) 42A4A2 (murine IgG1 against NHBA)
(B) MAb502 (murine IgG2a against fHbp)
(C) 12C1/D7 (murine IgG2b against fHbp)
(D) 11F10/G6 (murine IgG2b against fHbp)
(E) 9F11/19 antibody (murine IgG2b against NadA)
(F) Anti-PorA(P1.4), available from NIBSC.

These antibodies are bactericidal, except for 42A4A2 (which is non-bactericidal but seems to recognise a conformational epitope).

The BEXSERO™ product is serially diluted 9 times, either 1:2 or 1:5 each time. Six of these dilution series are present in rows (A) to (F) of a first microtitre plate (plate 1), from columns 1 (strongest) to 10 (most dilute). Each row receives one of the six monoclonal antibodies (A) to (F) described above, each used at the same strength in each column. After incubation the contents of these 60 wells are transferred into 60 wells in a second plate (plate 2). The wells in rows (A) to (F) in plate 2 are coated with the individual recombinant proteins (A) NHBA (B-D) fHbp (E) NadA and (F) PorA. In other embodiments, all wells in a single ELISA plate are coated using the same antigen, and each antigen is tested separately by using a different ELISA microtiter plate.

The mixture is incubated for 2 hours at 37° C. (for fHbp) or at room temperature (for NHBA, NadA and PorA), then washed. Monoclonal antibodies which were unbound to the vaccine antigens are retained on the plates. Anti-mouse IgG, conjugated to alkaline phosphatase, is then added to all 60 wells with pNPP and the amount of retained monoclonal antibody is assessed by $OD_{405-620\ nm}$. Thus the vaccine immunogen (serially diluted) inhibits the binding of the monoclonal antibodies to the immobilised antigens in plate 2. Higher levels of epitope in the vaccine sample will lead to more inhibition of this binding, and thus to less detectable signal after adding the pNPP.

FIGS. 1A to 1F show the results from the six rows. The graphs also include data measured with a reference vaccine, and comparison of the two parallel lines reveals the following relative potencies:

|      | A     | B     | C     | D     | E     | F     |
|------|-------|-------|-------|-------|-------|-------|
| R.P. | 0.915 | 2.344 | 0.859 | 0.895 | 1.037 | 1.033 |

Figure 1B:
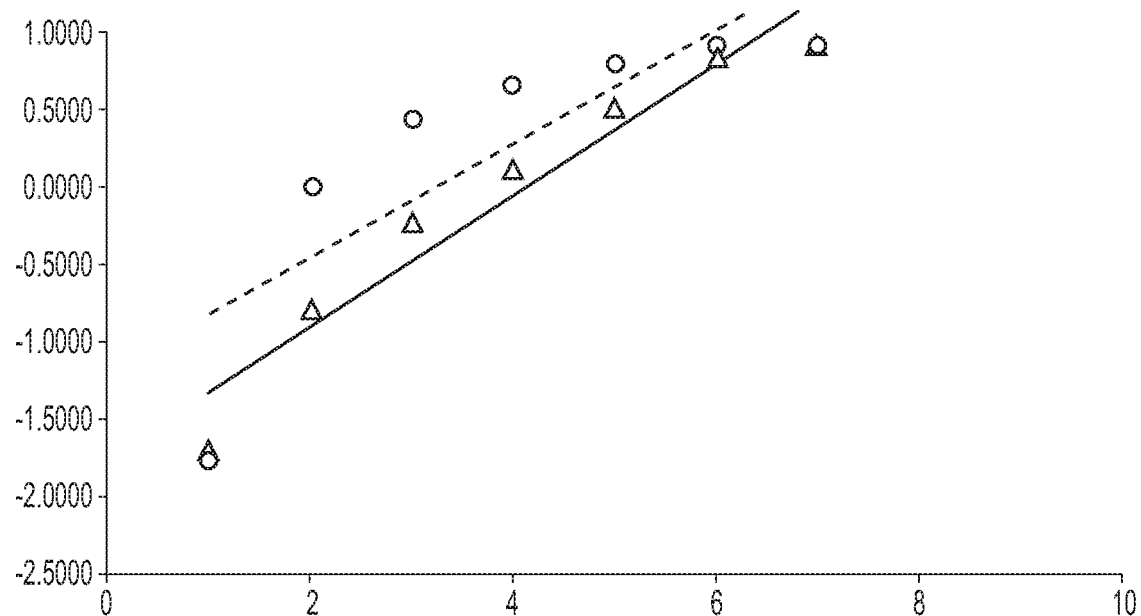
Figure 1C:
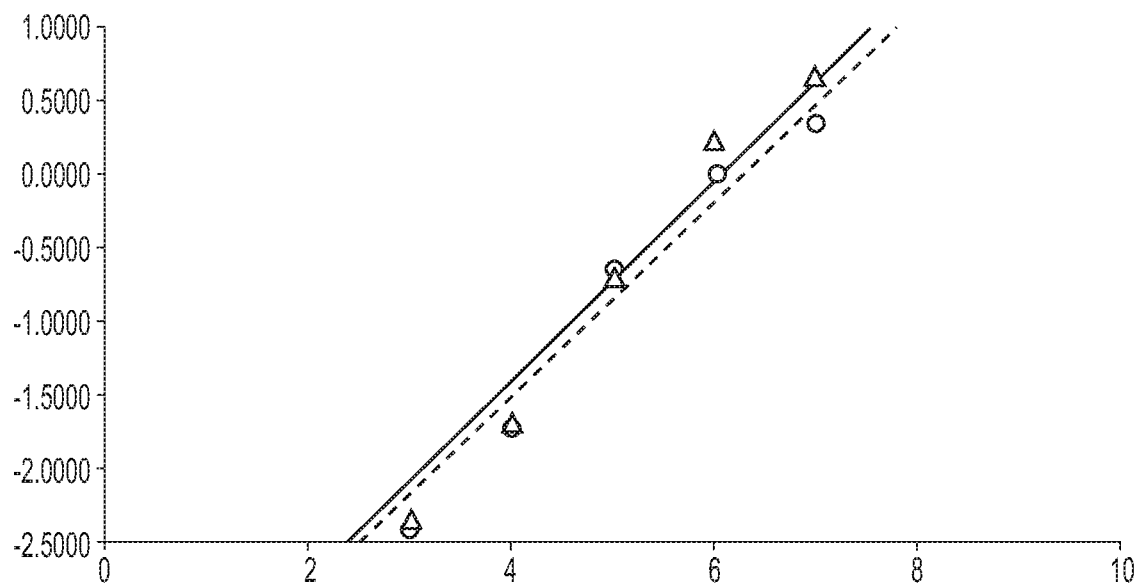
Figure 1D:
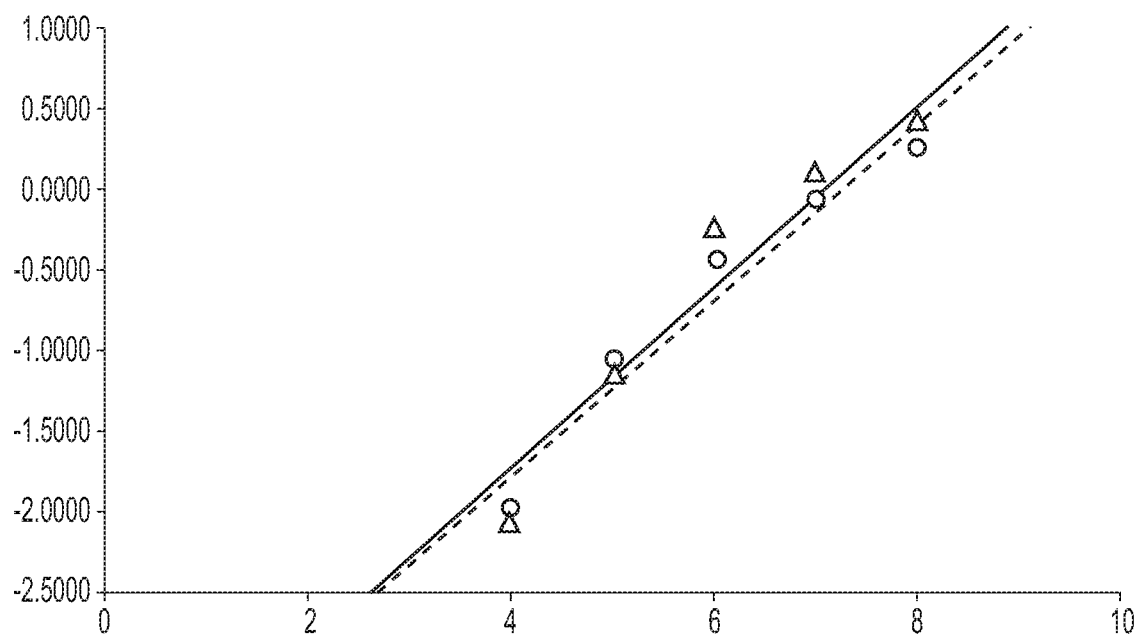
Figure 1E:
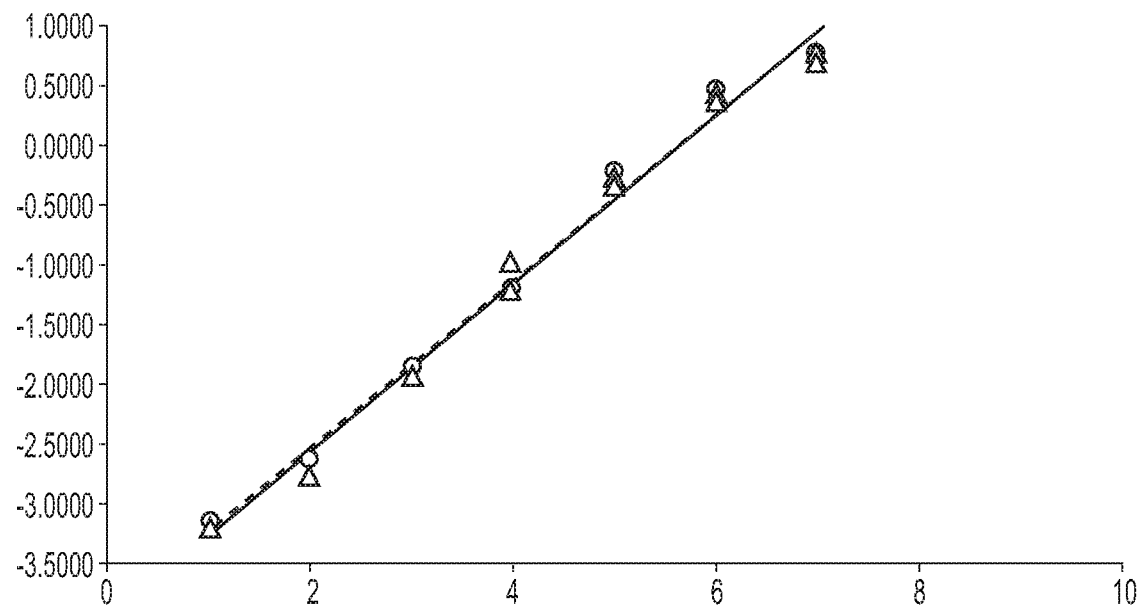

The aberrant value in FIG. 1B (i.e. using MAb502) arose because the curves were not linear and were not parallel to each other. In all other cases the curves were linear with good $R^2$ values. Thus the assay is suitable for assessing relative potency.

Figure 1F:
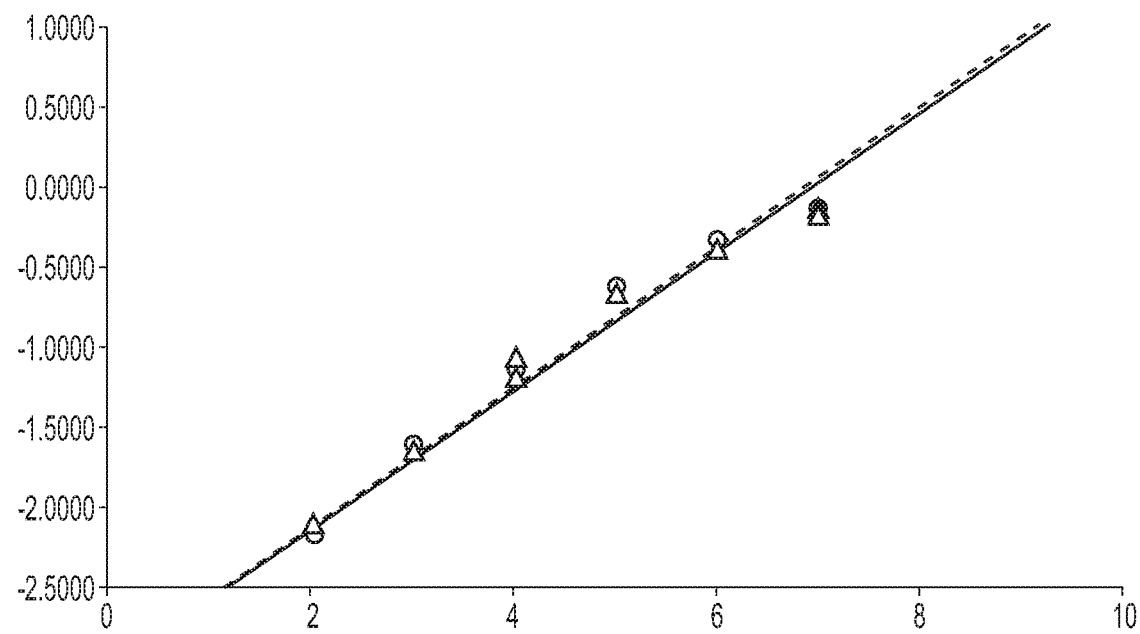
Figure 2A:
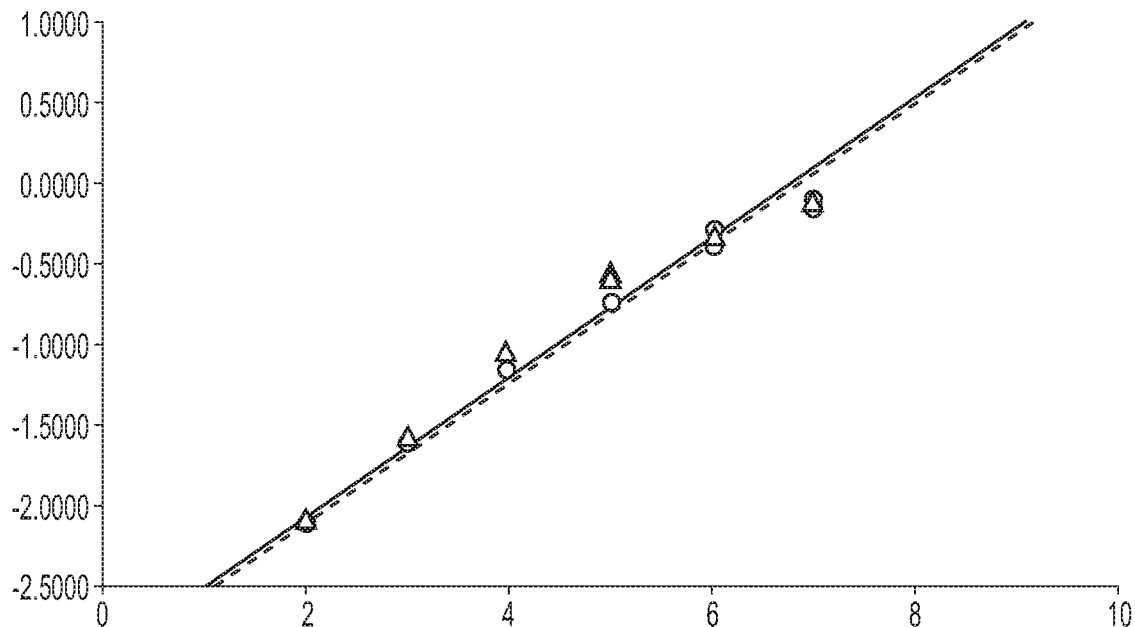
FIG. 2 shows relative potency plots for two further batches of OMV in BEXSERO™.
Figure 2B:
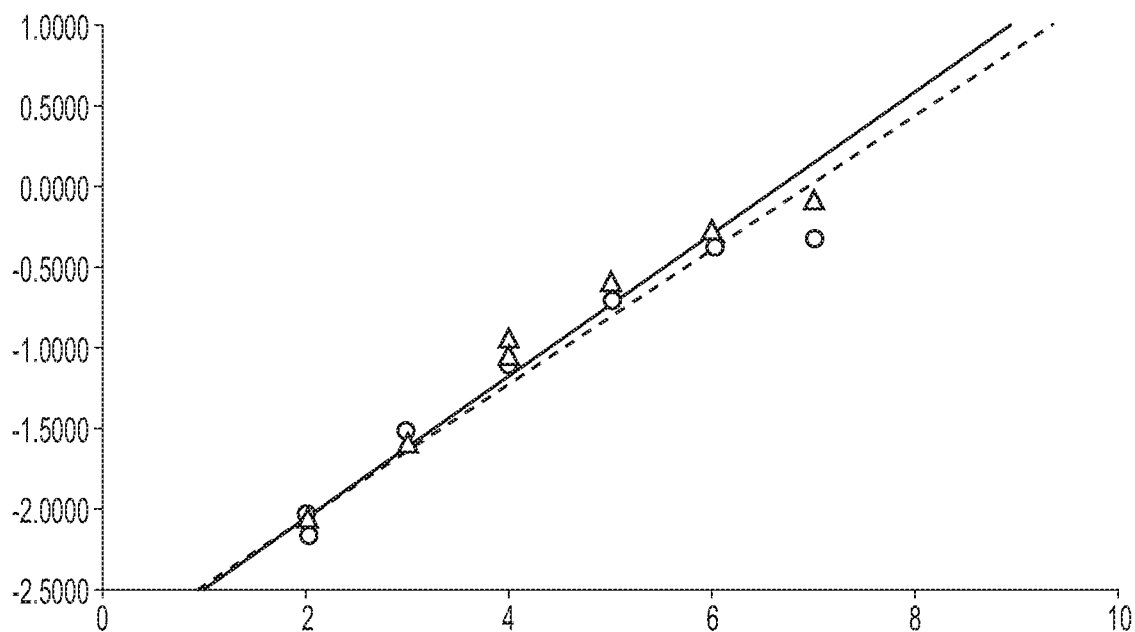

To check for inter-assay consistency the anti-PorA measurement was checked for two further BEXSERO™ batches (FIGS. 2A and 2B). The results in FIGS. 1F, 2A and 2B show no big differences, and RP was 1.033, 0.917 and 0.893 in the three different vaccine batches.

The ability of this assay to identify damaged vaccine was tested by artificially exposing a BEXSERO™ product to thermal stress. Relative potency values for each of the four immunogen components after 2 hours at 80° C. were as follows:

|      | NHBA | fHbp | NadA | OMV  |
|------|------|------|------|------|
| R.P. | 0.25 | 0.08 | 0.01 | 0.55 |

Figure 3:
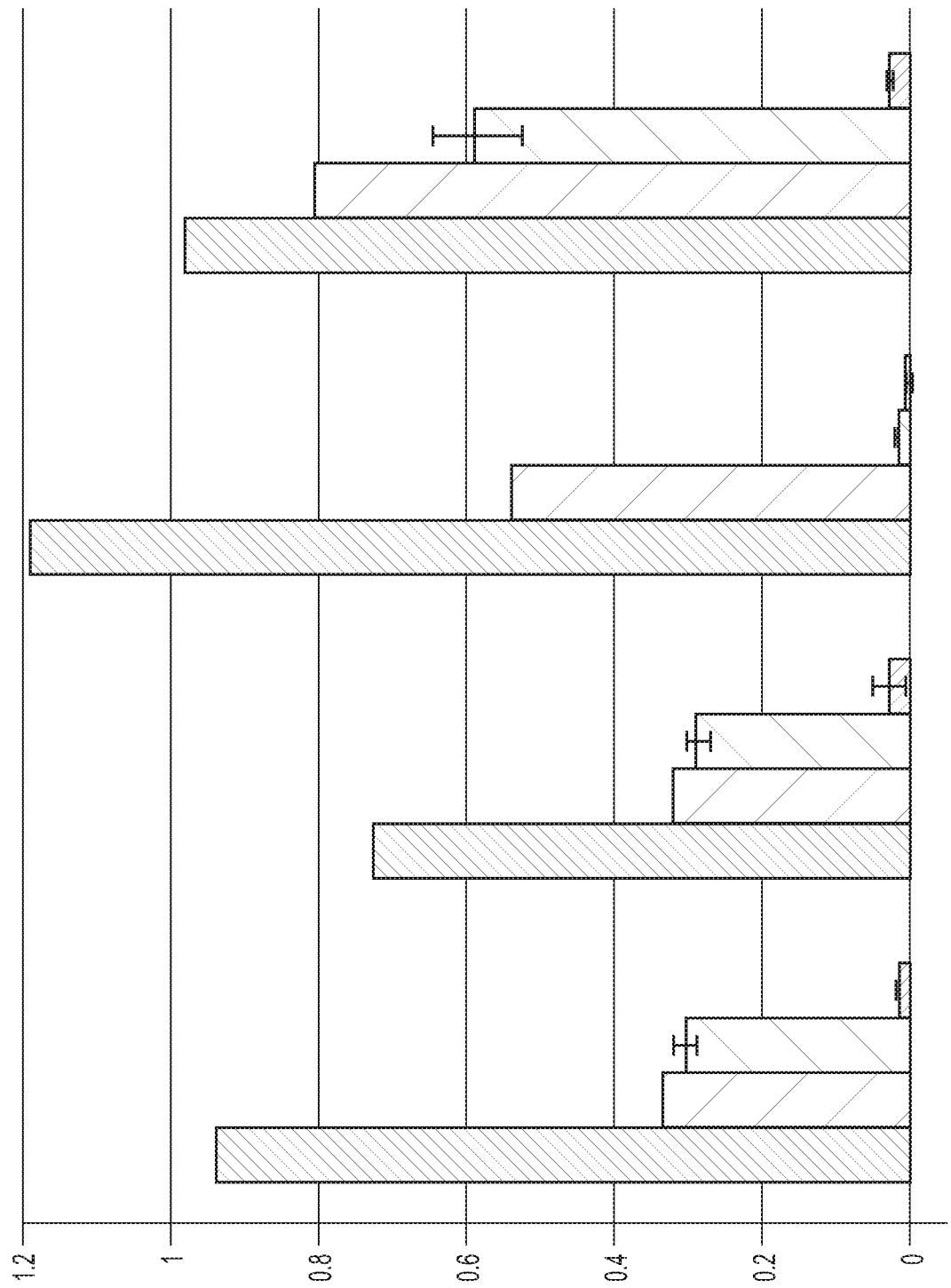
FIG. 3 shows RP values for vaccines heated overnight. The four groups of four bars are, from left to right: fHbp; NHBA; NadA; and OMVs. Within each group, the four bars are: 37° C.; 50 C; 60° C.; and 80° C.
Figure 4A:
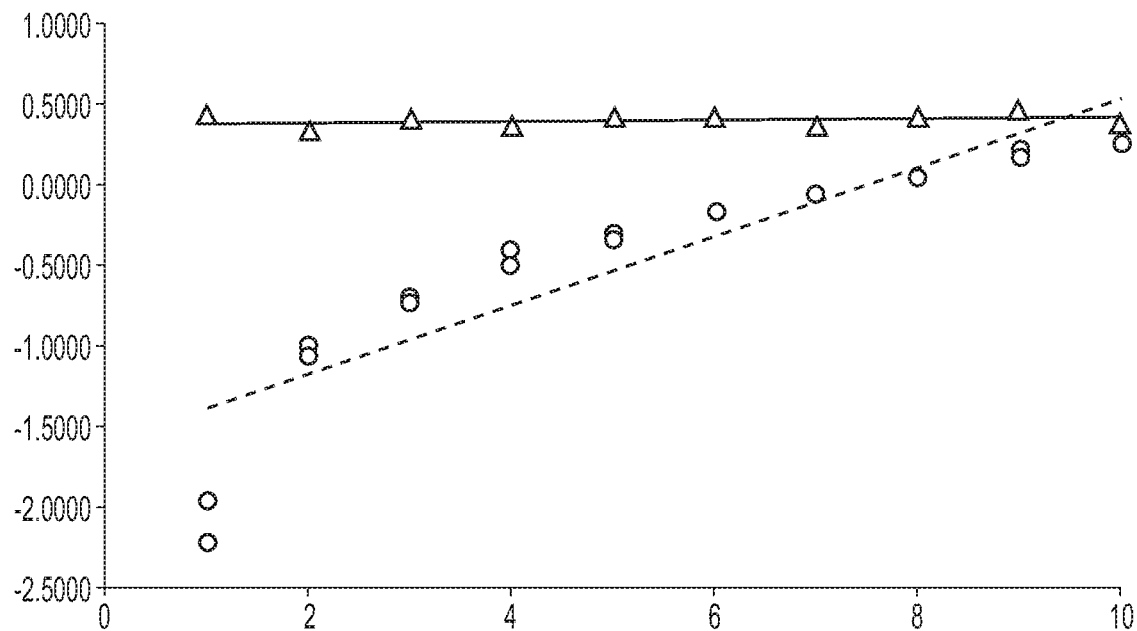
FIG. 4 shows RP plots for standard vaccine (circles) and for adjuvant (triangles) using monoclonal antibodies (A) MAb502 (B) 42A4A2 (C) 9F11/19 and (D) Anti-PorA.
Figure 4B:
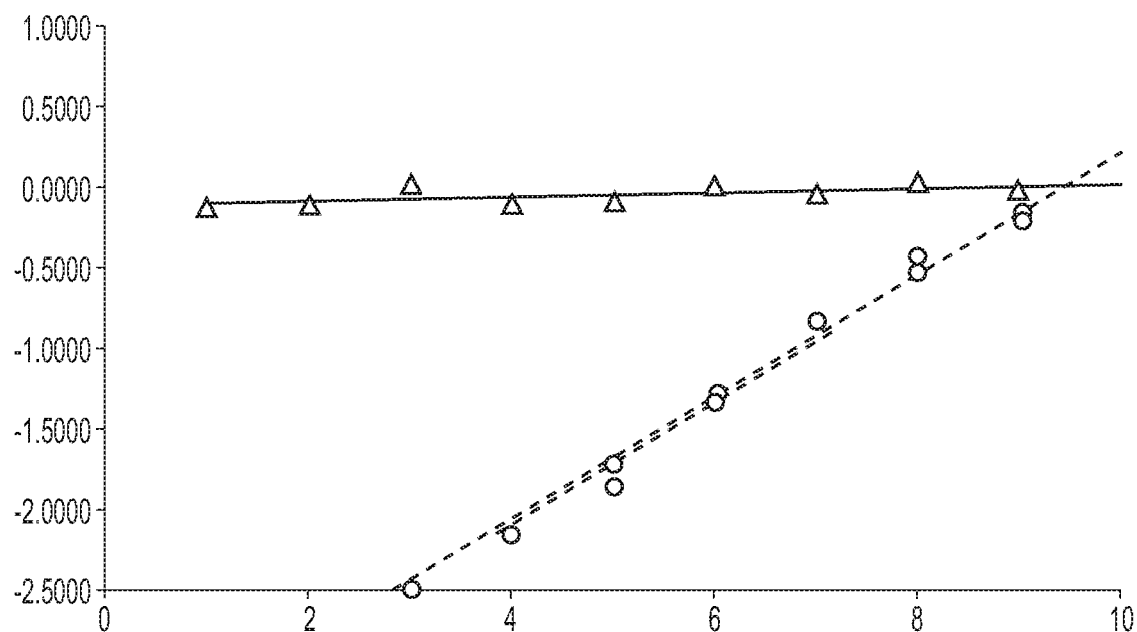
Figure 4C:
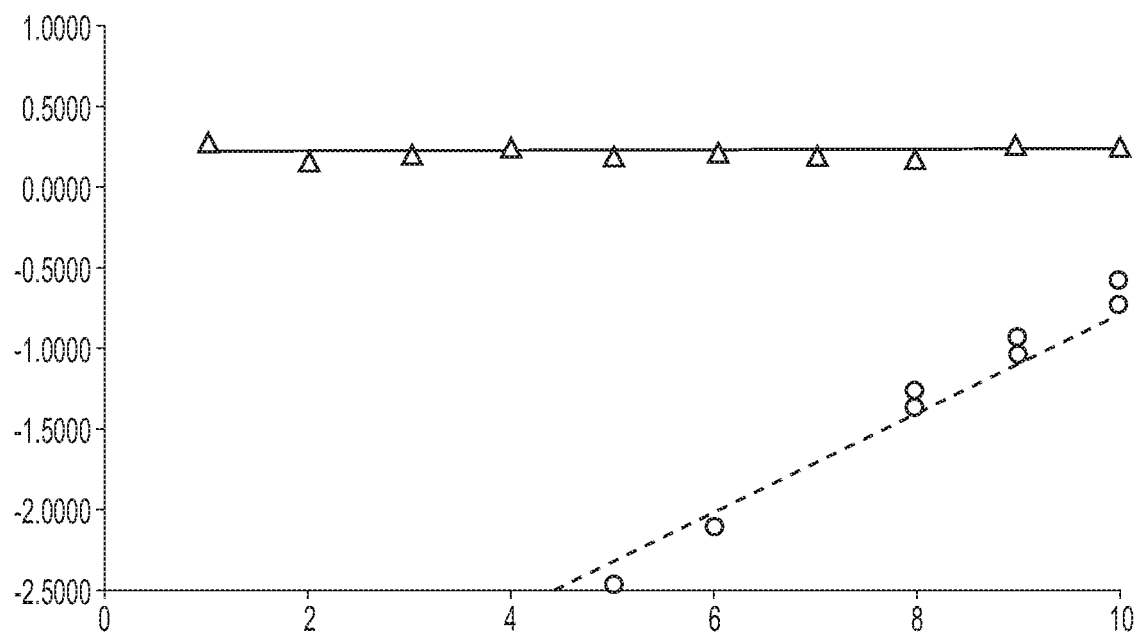
Figure 4D:
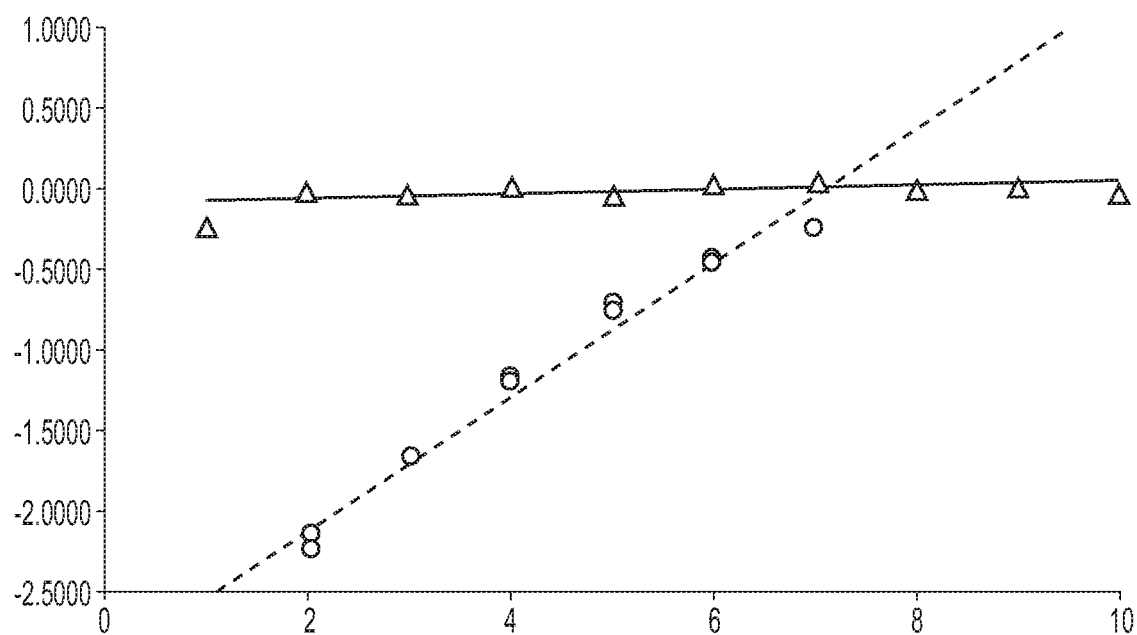
Figure 5:
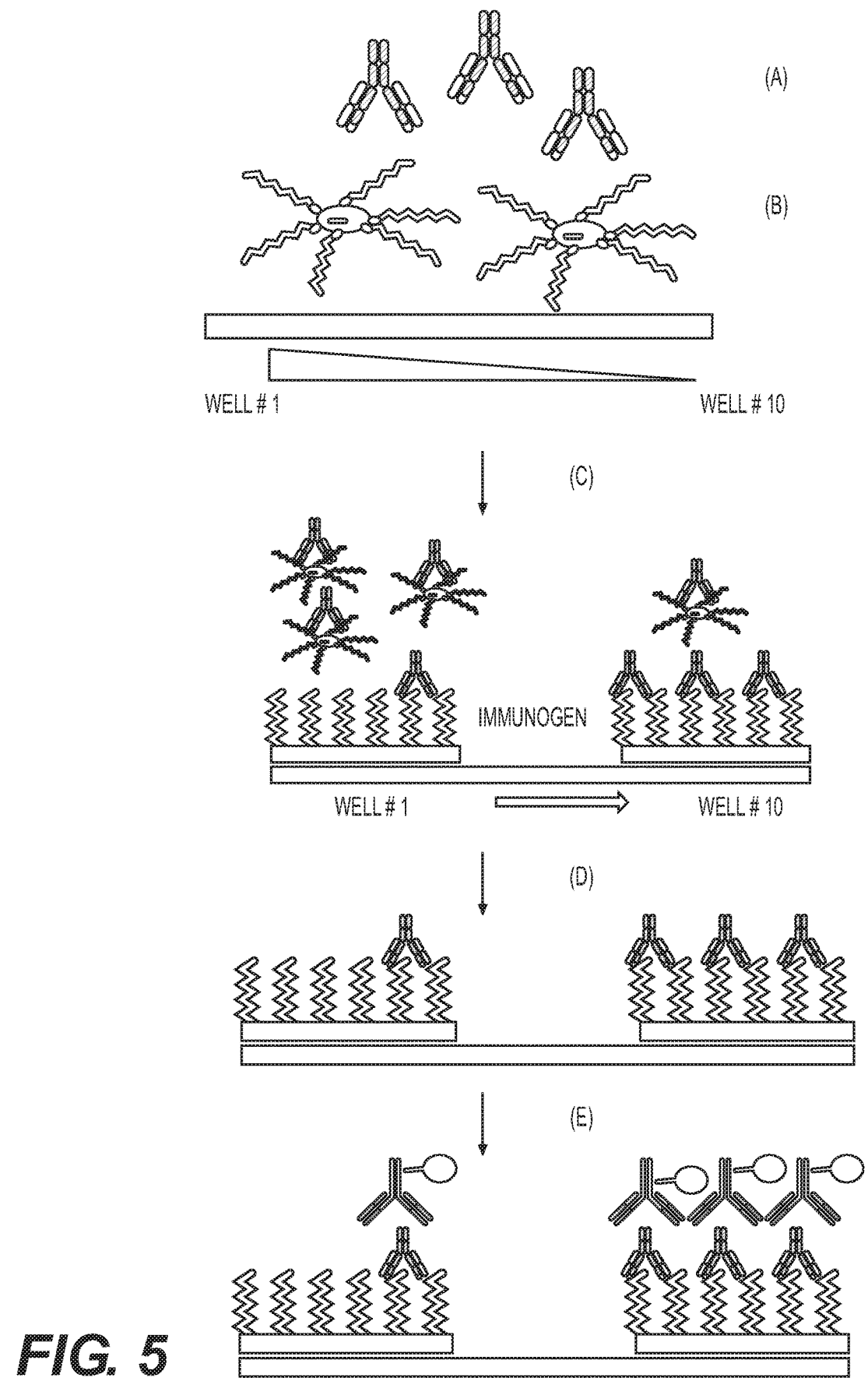
FIG. 5 illustrates an ELISA of the invention in competitive format. At the top, monoclonal antibody (A) for one of the vaccine immunogens is mixed with the vaccine sample (B) in ten wells having increasingly-diluted vaccine in each well. In (C) this mixture is transferred into the wells of a second plate, the wells of which are coated with immobilised vaccine immunogen. After incubation the plates are washed (D), then enzyme-conjugated anti-mAb serum is added in step (E), after which the enzyme is used to catalyse a detectable reaction for ELISA output.

FIG. 3 shows relative potency values for each of the four immunogen components after overnight incubation at 37° C., 50° C., 60° C. and 80° C. Thus the assay can detect losses in potency caused by thermal mistreatment.

To confirm that the aluminium hydroxide adjuvant did not interfere with the assay, antibodies (A), (B), (E) and (F) were tested with standard vaccine or with adjuvant. As shown in FIG. 4, the adjuvant always showed its inability to compete and/or interfere with the binding of each monoclonal antibody to the respective immunogen(s).

Anti fHbp Monoclonal Antibodies

Four bactericidal murine anti-fHbp IgG2b subclass monoclonal antibodies were obtained: 12C1/D7; 11F10/G6; 30G11/H3; and 14B3/D4. RNA was isolated from the murine hybridoma cells using an Oligotex Direct mRNA Mini Kit according to the manufacturer's instructions. cDNA was produced via reverse transcription using ~200 ng of the poly(A)+RNA template, an oligo-(dT) primer, and SuperScript II RT. cDNA was amplified by PCR using immunoglobulin heavy (H)- and light (L)-chain degenerate primers as described in reference 86. The purified products were inserted into the pSTBlue-1 Perfectly Blunt vector for sequencing.

12C1/D7's $V_L$ region has amino acid sequence
SEQ ID NO: 21:
DIVLTQSPSSIYASLGERVTLTCKASQDIHNYLNWFQQKPGKSPKTLIYR

ANRLVDGVPSRFSGGGSGQDYSLTISSLEFEDIGIYYCLQYDEFPPTFGG

GTRLEIKRADAAPTVS and its $V_H$ region has amino acid sequence
SEQ ID NO: 22:
QVQLQESGPELVKPGASVKISCKASGYSFSDYNMSWVKQSNGKSLEWIGI

IDPKYGTINYNQKFKGKATLTVDQASSTAYMQLNSLTSEDSAVYYCVRDY

YGSSYFDYWGQGTTLTVS

11F10/G6's $V_L$ region has amino acid sequence
SEQ ID NO: 23:
DIVLTQTPSSIYASLGERVTLTCKASQDIHNYLNWFQQKPGKSPKTLIYR

ANRLVDGVPSRFSGGGSGQDYSLTISSLEFEDIGIYYCLQYDEFPPTFGG

GTRLEIKRADAAPTVS and its $V_H$ region has amino acid sequence
SEQ ID NO: 24:
EFQLQQSGPELVKPGASVKISCKASGYSFSDYNMSWVKQSNGKSLEWIGI

IDPKYGTINYNQKFKGKATLTVDQASSTAYMQLNSLTSEDSAVYYCVRDY

YGSSYFDYWGQGTTLTVS

-continued

30G11/H3's $V_L$ region has amino acid sequence
SEQ ID NO: 25:
DIVMTQSQKFMSTSVGDRVSITCKASQHVRTAVAWYQQKPGQSPKGLIYL

ASNRRTGVPDRFTASGSGTDFTLTITNVQSEDLADYFCLQHWNYPFTFGS

GTKLEIKRADAAPTVS and its $V_H$ region has amino acid sequence
SEQ ID NO: 26:
EVQLEESGPELVKPGASVKISCKASGYSFSDYNMSWVKQSNGKSLEWIGI

IDPKYGTINYNQKFKGKATLTVDQASSTAYMQLNSLTSEDSAVYYCVRDY

YGSSYFDYWGQGTTLTVS

14B3/D4's $V_L$ region has amino acid sequence
SEQ ID NO: 27:
DIVLTQSPSSLTVTAGEKVTMSCRSSQSLLNSGNQKNYLTWYQQKPGQPP

KLLIYWASTRESGVPDRFTGSGSGTDFTLTISSVQAEDLAIYYCQNDYNY

PLTFGAGTKLELKR and its $V_H$ region has amino acid sequence
SEQ ID NO: 28:
QVQLQQPGAELVKPGASVKLSCKASGYSFTTYYWMNWVKQRPGQGLEWIG

MIHPNSGSTNYNEKFKNKATLTVDKSSSTAYIQLSSLTSEDSAVFYCAAH

YNKYEGYFYAMDYWGQGTSVTVSS

In a FACS assay the 11F10/G6 and 30G11/H3 were able to bind to meningococcal strains having each of the three different fHbp variants: MC58 (variant 1); 961-5945 (variant 2); and M1239 (variant 3). Moreover, these two FACS-positive antibodies also showed bactericidal activity against strains having each of the three variants.

14B3/D4 was FACS-positive and bactericidal against MC58 and 961-5945, but not against M1239. 12C1/D7 was FACS-positive and bactericidal against MC58, but not against 961-5945 or M1239. 12C1/D7 and 11F10/G6 competed with fH for binding to fHbp; the other two antibodies did not.

The epitope for 11F10/G6 seems to include residue Lys-268 in fHbp (var 1.1).

The epitope for 12C1/D7 seems to include residue Val-270 in fHbp (var 1.1).

The epitope for 14B3/D4 seems to include residues 60-90 in fHbp.

The epitope for 30H11/H3 seems to include residue Lys-257 in fHbp (var 1.1).

It will be understood that the invention is described above by way of example only and modifications may be made whilst remaining within the scope and spirit of the invention.

REFERENCES

[1] Metz et al. (2002) *Vaccine* 20:2411-30.
[2] Donnelly et al. (2010) *PNAS USA* 107:19490-5.
[3] US-2010/0035234.
[4] U.S. Pat. No. 7,510,687.
[5] WO2007/066231.
[6] Poulsen & Jensen (2007) *J Biomol Screen* 12:240-7.
[7] Bai et al. (2011) *Expert Opin Biol Ther.* 11:969-85.
[8] Giuliani et al. (2006) *PNAS USA* 103:10834-9.
[9] Marsh et al. (2011) *Vaccine* 29:6049-58.
[10] WO02/09643.
[11] Katial et al. (2002) *Infect. Immun.* 70:702-707.
[12] U.S. Pat. No. 6,180,111.
[13] WO01/34642.
[14] WO2006/046143.
[15] WO2004/019977.
[16] European patent 0011243.
[17] Fredriksen et al. (1991) *NIPH Ann.* 14(2):67-80.
[18] WO01/91788.
[19] WO2005/004908.
[20] WO2011/036562.
[21] Claassen et al. (1996) *Vaccine* 14:1001-8.
[22] de Kleijn et al. (2000) *Vaccine* 18:1456-66.
[23] WO03/105890.
[24] WO2006/024946
[25] Tettelin et al. (2000) *Science* 287:1809-1815.
[26] Gennaro (2000) *Remington: The Science and Practice of Pharmacy.* 20th edition, ISBN: 0683306472.
[27] *Vaccine Design* . . . (1995) eds. Powell & Newman. ISBN: 030644867X. Plenum.
[28] Borrow et al. (2006) *Vaccine.* 24:5093-107.
[29] Rodriguez et al. (2002) *Clin Vaccine Immunol* 9:109-14.
[30] Borrow & Carlone (2001) *Methods in Molecular Medicine* 66:289-304.
[31] Martin et al. (2005) *Vaccine* 23:2218-21.
[32] Borrow et al. (2005) *Clin Diag Lab Immunol* 12:970-6.
[33] WO2009/150531.
[34] Scarselli et al. (2009) *J Mol Biol* 386:97-108.
[35] Welsch et al. (2004) *J Immunol* 172:5606-15.
[36] Beernink et al. (2009) *Molecular Immunology* 46:1647-53.
[37] Giuntini et al. (2011) *Infect. Immun.* 79:3751-9.
[38] *Methods In Enzymology* (S. Colowick and N. Kaplan, eds., Academic Press, Inc.)
[39] *Handbook of Experimental Immunology*, Vols. I-IV (D. M. Weir and C. C. Blackwell, eds, 1986, Blackwell Scientific Publications)
[40] Sambrook et al. (2001) *Molecular Cloning: A Laboratory Manual,* 3rd edition (Cold Spring Harbor Laboratory Press).
[41] *Handbook of Surface and Colloidal Chemistry* (Birdi, K. S. ed., CRC Press, 1997)
[42] Ausubel et al. (eds) (2002) *Short protocols in molecular biology,* 5th edition (Current Protocols).
[43] *Molecular Biology Techniques: An Intensive Laboratory Course*, (Ream et al., eds., 1998, Academic Press)
[44] *PCR* (*Introduction to Biotechniques Series*), 2nd ed. (Newton & Graham eds., 1997, Springer Verlag)
[45] Geysen et al. (1984) *PNAS USA* 81:3998-4002.
[46] Carter (1994) *Methods Mol Biol* 36:207-23.
[47] Jameson, B A et al. 1988, *CABIOS* 4(1):181-186.
[48] Raddrizzani & Hammer (2000) *Brief Bioinform* 1(2):179-89.
[49] Bublil et al. (2007) *Proteins* 68(1):294-304.
[50] De Lalla et al. (1999) *J. Immunol.* 163:1725-29.
[51] Kwok et al. (2001) *Trends Immunol* 22:583-88.
[52] Brusic et al. (1998) *Bioinformatics* 14(2):121-30
[53] Meister et al. (1995) *Vaccine* 13(6):581-91.
[54] Roberts et al. (1996) *AIDS Res Hum Retroviruses* 12(7):593-610.
[55] Maksyutov & Zagrebelnaya (1993) *Comput Appl Biosci* 9(3):291-7.
[56] Feller & de la Cruz (1991) *Nature* 349(6311):720-1.
[57] Hopp (1993) *Peptide Research* 6:183-190.
[58] Welling et al. (1985) *FEBS Lett.* 188:215-218.
[59] Davenport et al. (1995) *Immunogenetics* 42:392-297.
[60] Tsurui & Takahashi (2007) *J Pharmacol Sci.* 105(4):299-316.
[61] Tong et al. (2007) *Brief Bioinform.* 8(2):96-108.
[62] Schirle et al. (2001) *JImmunol Methods.* 257(1-2):1-16.

[63] Chen et al. (2007) *Amino Acids* 33(3):423-8.
[64] *Current Protocols in Molecular Biology* (F. M. Ausubel et al., eds., 1987) Supplement 30
[65] Smith & Waterman (1981) *Adv. Appl. Math.* 2: 482-489.
[66] WO00/66741.
[67] WO99/57280
[68] Serruto et al. (2010) *PNAS USA* 107:3770-5.
[69] U.S. Pat. No. 5,698,438.
[70] WO2010/070453.
[71] Perkins-Balding et al. (2003) *Microbiology* 149:3423-35.
[72] Masignani et al. (2003) *J Exp Med* 197:789-799.
[73] Welsch et al. (2004) *J Immunol* 172:5605-15.
[74] Hou et al. (2005) *J Infect Dis* 192(4):580-90.
[75] WO03/063766.
[76] Fletcher et al. (2004) *Infect Immun* 72:2088-2100.
[77] Zhu et al. (2005) *Infect Immun* 73(10):6838-45.
[78] Cantini et al. (2006) *J. Biol. Chem.* 281:7220-7227
[79] WO2004/048404
[80] WO2009/104097.
[81] Martin et al. (1997) *J Exp Med* 185(7):1173-83.
[82] WO96/29412.
[83] WO01/55182.
[84] WO01/38350.
[85] WO00/23595.
[86] Wang et al. (2000) *J. Immunol. Meth.* 233:167-77.

The invention claimed is:

1. A method of assessing relative potency in vitro of a batch of vaccine or a bulk vaccine comprising the steps of:

(i) taking a sample from the batch of vaccine or the bulk vaccine comprising a meningococcal protein immunogen, wherein the meningococcal protein immunogen is factor H binding protein (fHbp);

(ii) contacting the sample with a monoclonal antibody wherein the monoclonal antibody (a) $V_L$ region has the amino acid sequence of SEQ ID NO: 21 and $V_H$ region has the amino acid sequence of SEQ ID NO: 22, (b) $V_L$ region has the amino acid sequence of SEQ ID NO: 23 and $V_H$ region has the amino acid sequence of SEQ ID NO: 24, (c) $V_L$ region has the amino acid sequence of SEQ ID NO: 25 and $V_H$ region has the amino acid sequence of SEQ ID NO: 26, or (d) $V_L$ region has the amino acid sequence of SEQ ID NO: 27 and $V_H$ region has the amino acid sequence of SEQ ID NO: 28; then (iii) measuring immunospecific binding of the meningococcal protein immunogen to the monoclonal antibody; then (iv) comparing the measurement from step (iii) to a measurement obtained by (1) having contacted a standard vaccine sample comprising the meningococcal protein immunogen of known in vivo potency with the monoclonal antibody; then (2) having measured binding of the meningococcal protein immunogen in the standard vaccine sample to the monoclonal antibody to determine the potency of the batch of vaccine or the bulk vaccine relative to the potency of the standard vaccine sample.

2. The method of claim 1, wherein the measuring the binding comprises quantitatively detecting the meningococcal protein immunogen in the sample.

3. The method of claim 1, wherein the binding is measured by competitive ELISA.

4. The method of claim 3, wherein the competitive ELISA comprises contacting the sample in the presence of a competitor antigen attached to a solid surface, wherein the competitor antigen binds to the monoclonal antibody.

5. The method of claim 1, further comprising contacting the monoclonal antibody with a secondary antibody labelled with an enzyme.

6. The method of claim 1, wherein the contacting is performed in a microwell plate.

7. The method of claim 1, wherein the sample further comprises meningococcal Neisserial Heparin Binding Antigen (NHBA) or meningococcal Neisserial adhesin A (NadA).

8. The binding assay of claim 1, wherein the sample further comprises a meningococcal vesicle.

9. The method of claim 1, wherein the meningococcal protein immunogen is adsorbed to an aluminum salt adjuvant.

10. The method of claim 1, wherein the monoclonal antibody is the only monoclonal antibody used in step (ii).

11. The method of claim 1, wherein the monoclonal antibody is a murine monoclonal IgG antibody.

* * * * *